United States Patent
Watanabe

(10) Patent No.: US 9,017,261 B2
(45) Date of Patent: Apr. 28, 2015

(54) ULTRASONIC DIAGNOSTIC APPARATUS AND BEAMFORMING METHOD

(71) Applicant: Konica Minolta, Inc., Tokyo (JP)

(72) Inventor: Yasuhito Watanabe, Osaka (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 14/083,857

(22) Filed: Nov. 19, 2013

(65) Prior Publication Data
US 2014/0094700 A1 Apr. 3, 2014

Related U.S. Application Data

(63) Continuation of application No. PCT/JP2013/003461, filed on May 31, 2013.

(30) Foreign Application Priority Data

Jun. 4, 2012 (JP) .................................. 2012-126768

(51) Int. Cl.
 *A61B 8/00* (2006.01)
 *G01S 7/52* (2006.01)
 *G10K 11/34* (2006.01)

(52) U.S. Cl.
 CPC .............. *A61B 8/44* (2013.01); *G01S 7/52085* (2013.01); *G01S 7/52047* (2013.01); *G10K 11/346* (2013.01); *G10K 11/348* (2013.01)

(58) Field of Classification Search
 CPC ... A61B 8/44; G01S 7/52047; G01S 7/52085; G10K 11/346; G10K 11/348
 USPC .................... 382/131, 128, 254, 437; 600/437
 See application file for complete search history.

(56) References Cited

U.S. PATENT DOCUMENTS 8,045,777 B2 10/2011 Zwirn
2007/0047743 A1 3/2007 Taenzer et al.
(Continued)

FOREIGN PATENT DOCUMENTS

| JP | 10-127635 | 5/1998 |
|---|---|---|
| JP | 2008-526291 | 7/2008 |
| JP | 2009-506683 | 2/2009 |
| WO | 2006/070362 | 7/2006 |
| WO | 2007/025265 | 3/2007 |
| WO | 2011/057252 | 5/2011 |

OTHER PUBLICATIONS

Written Opinion of the International Searching Authority issued in International Application No. PCT/JP2013/003461 on Jun. 25, 2013.
(Continued)

*Primary Examiner* — Elmer Chao
(74) *Attorney, Agent, or Firm* — Holtz, Holtz, Goodman & Chick PC

(57) ABSTRACT

An ultrasonic diagnostic apparatus includes: a first reference beam generating unit generating a first reference beam from DAS signals calculated in an N-th frame; a second reference beam generating unit generating a second reference beam from a DAS signal calculated in an (N−1)-th frame, the DAS signal calculated in the N-th frame, and another DAS signal calculated in an (N+1)-th frame; an attenuation coefficient calculating unit calculating, based on the first reference beam and the second reference beam, an attenuation coefficient to be multiplied by the DAS signals calculated in the N-th frame; and a beamforming unit generating and providing a beamformed signal generated for a reference scan line in the N-th frame by multiplying a DAS signal calculated in the N-th frame by the attenuation coefficient.

12 Claims, 16 Drawing Sheets

(56) References Cited

U.S. PATENT DOCUMENTS

2008/0114253 A1   5/2008   Randall et al.
2008/0262352 A1   10/2008  Zwirn
2009/0141957 A1   6/2009   Yen et al.
2012/0157851 A1   6/2012   Zwirn
2012/0289835 A1   11/2012  Hwang

OTHER PUBLICATIONS

Masayasu Ito et al., "Chiyouompa shindan souchi (ultrasonic diagnostic device)" Corona Publishing Co., Ltd., 2002 with partial English translation.

International Search Report (in Japanese language) issued in International Application No. PCT/JP2013/003461 on Jun. 25, 2013.

ULTRASONIC DIAGNOSTIC APPARATUS AND BEAMFORMING METHOD

CROSS REFERENCE TO RELATED APPLICATIONS

This is a continuation application of PCT International Application No. PCT/JP2013/003461 filed on May 31, 2013, designating the United States of America, which is based on and claims priority of Japanese Patent Application No. 2012-126768 filed on Jun. 4, 2012. The entire disclosures of the above-identified applications, including the specifications, drawings and claims are incorporated herein by reference in their entirety.

FIELD

One or more exemplary embodiments disclosed herein relate generally to an ultrasonic diagnostic apparatus and, more particularly, to a beamforming method thereof.

BACKGROUND

Delay-and-sum (DAS) beamforming is a typical beamforming technique used for ultrasonic diagnostic apparatuses in order to process received ultrasound signals (see NPL 1).

CITATION LIST

Non Patent Literature

[NPL 1]
"Cho-ompa shindan souchi (ultrasonic diagnostic device)", Masayasu Ito, Takashi Mochizuki, CORONA PUBLISHING CO., LTD. Aug. 26, 2002, pp. 42-45)

SUMMARY

Technical Problem

An ultrasonic diagnostic apparatus usually executes a DAS operation once to generate an ultrasound image for one scan line. A possible technique to improve the resolution of the image involves executing multiple DAS operations for the one scan line and a scan line neighboring the one scan line. The DAS operation, however, involves processing many signals. A question which comes with multiple DAS operations is how to reduce the amount of the calculations to decrease the loads of the signal processing.

One non-limiting and exemplary embodiment provides an ultrasonic diagnostic apparatus which is capable of reducing signal processing loads as well as improving the resolution of images.

Solution to Problem

In one general aspect, the techniques disclosed here feature an ultrasonic diagnostic apparatus. The ultrasonic diagnostic apparatus includes a beamformer which generates beamformed signals, each corresponding to one of scan lines for generating an ultrasound image, from echo signals generated from ultrasound signals bounced off a subject and received by receiving elements. The beamformer includes: a delay-and-sum (DAS) unit configured, for each of frames, to (i) determine one of the scan lines, in a sorting order determined in a given direction, as a target scan line for the frame and select 2k+1 scan lines (k is a positive integer) included in the scan lines and aligned in a row with the target scan line positioned in a middle, and (ii) perform a DAS operation on each of the echo signals to calculate a first DAS signal which is a DAS signal for the target scan line and second DAS signals which are DAS signals each for one of the selected 2k+1 scan lines other than the target scan line; a first reference beam generating unit which generates a first reference beam from the first DAS signal and the second DAS signals all of which are calculated in an N-th frame of the frames; a second reference beam generating unit which generates a second reference beam from (i) one of the second DAS signals which is calculated in an (N−1)-th frame of the frames immediately preceding the N-th frame and is generated for one of the scan lines which has an earliest number in the sorting order, (ii) the first DAS signal which is calculated in the N-th frame and (iii) another one of the second DAS signals which is calculated in an (N+1)-th frame of the frames immediately succeeding the N-th frame and is generated for another one of the scan lines which has a latest number in the sorting order; an attenuation coefficient calculating unit which calculates, based on the first reference beam and the second reference beam, an attenuation coefficient for forming narrower a profile of the first DAS signal calculated in the N-th frame; and a beamforming unit which generates and provide a beamformed signal included in the beamformed signals and generated for the target scan line in the N-th frame, by multiplying the first DAS signal calculated in the N-th frame by the attenuation coefficient.

General and specific aspects disclosed above may be implemented using a system, a method, an integrated circuit, a computer program, or a computer-readable recording medium such as a CD-ROM, or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

An ultrasonic diagnostic apparatus according to one or more exemplary embodiments or features disclosed herein reduces an amount of the calculations as well as improving the resolution of an image.

BRIEF DESCRIPTION OF DRAWINGS

These and other advantages and features will become apparent from the following description thereof taken in conjunction with the accompanying Drawings by way of non-limiting examples of embodiments disclosed herein.

DESCRIPTION OF EMBODIMENTS

Underlying Knowledge Forming Basis of the Present Disclosure

Detailed first is the DAS beamforming described in the Background section.

Figure 1:
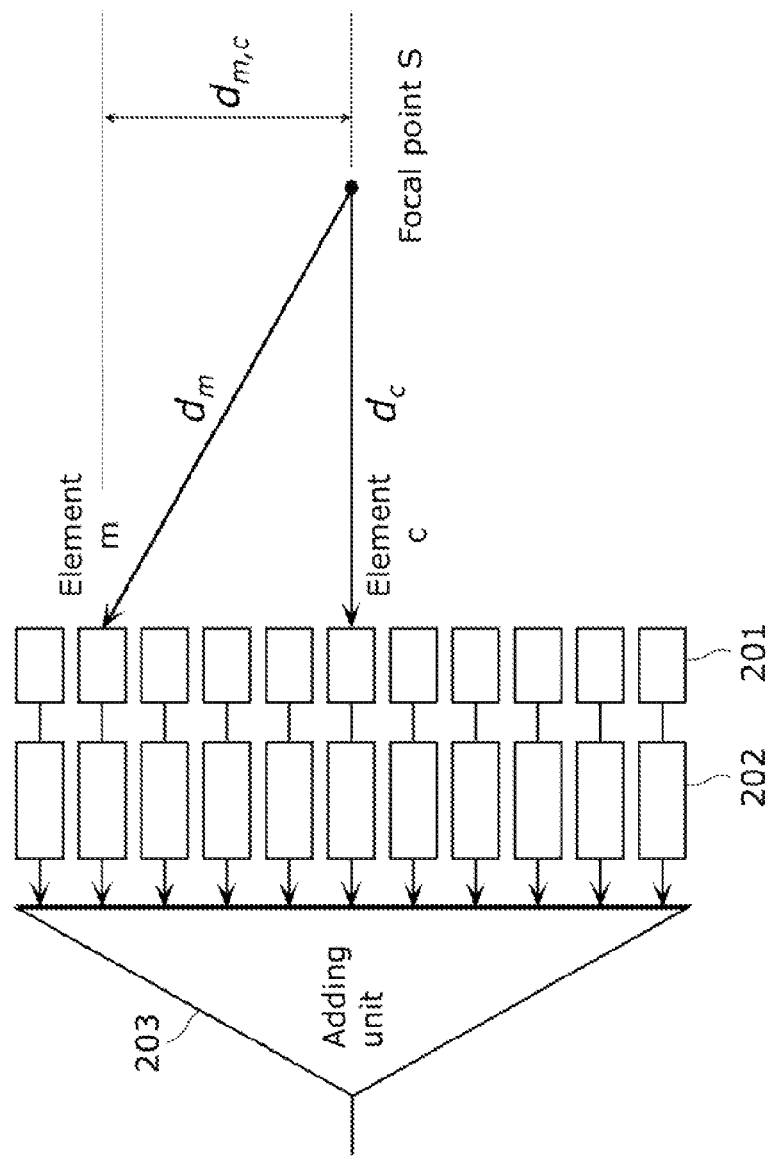
FIG. 1 schematically shows the DAS beamforming.

FIG. 1 schematically shows the DAS beamforming.

An ultrasonic diagnostic apparatus shown in FIG. 1 includes: multiple receiving elements 201 receiving ultrasound signals; delaying units 202 each provided to a corresponding one of the receiving elements 201 and delaying the ultrasound signals; and an adding unit 203 adding one another output signals from the delaying units.

In FIG. 1, for example, a not-shown transmitting unit is to emit (focus) ultrasound waves to a focal point S in a subject. The ultrasound waves emitted from the transmitting unit bounce off the subject and arrive at each of the receiving elements 201.

When the signals are bounced off the focal point S, for example, a bounced signal arrives at a receiving element c in the delay time dc and another bounced signal arrives at a receiving element m in the delay time dm.

In order to achieve phase matching between the two signals in the DAS beamforming, the signal received by the receiving element c is time-delayed by the subtraction of the delay time dc from the delay time dm. Then, in the DAS beamforming, the time-delayed signal (the signal received by the receiving element c) is added to the signal received by the receiving element m, and the signals are amplified.

In other words, the DAS beamforming involves time-delaying the signals received by the receiving elements 201 for each element, adding the time-delayed signals, and outputting the result of the addition from the adding unit 203.

A question which ultrasonic diagnostic apparatuses face is how to obtain ultrasound images in higher image quality in order to improve the accuracy of ultrasonic diagnoses.

An ultrasonic diagnostic apparatus usually executes a DAS operation once to generate an ultrasound image for one scan line. A possible technique to improve the resolution of the image involves executing multiple DAS operations for the one scan line and a scan line neighboring the one scan line.

Figure 2:
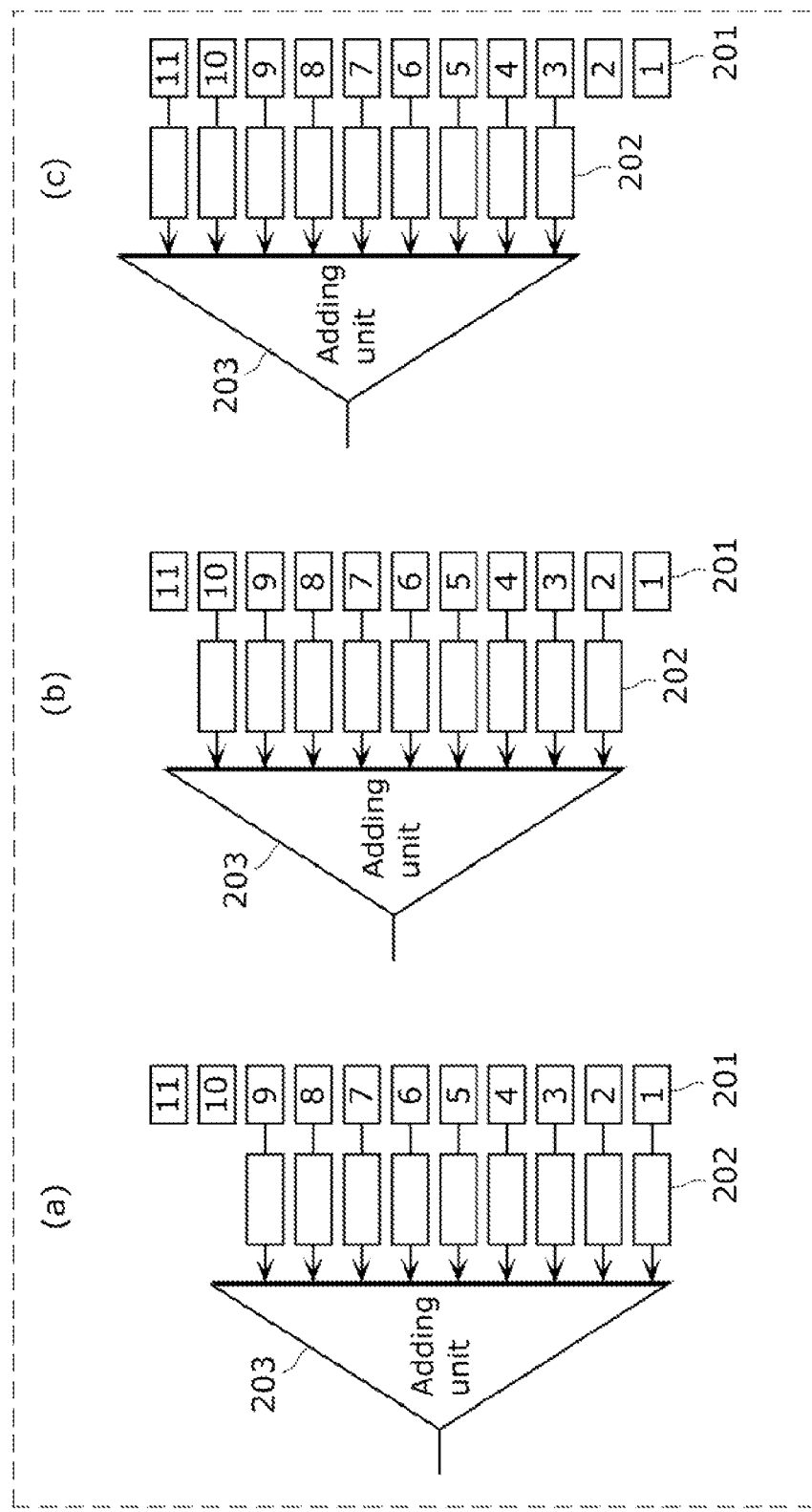
FIG. 2 illustrates how to obtain DAS signals for multiple scan lines.

FIG. 2 illustrates how to obtain DA signals for multiple scan lines.

When generated is an ultrasound image for a scan line corresponding to the fifth receiving element 201 shown in the illustration (a) in FIG. 2, ultrasound waves are emitted (transmitted) such that the fifth receiving element 201 is positioned in the middle. Then, as shown in the illustration (a) in FIG. 2, the first to ninth receiving elements 201 are used to perform DAS operations and a DAS signal for the fifth scan line is obtained with the fifth receiving element 201 positioned in the middle.

Similarly, as shown in the illustration (b) in FIG. 2, the second to tenth receiving elements 201 are used to obtain a DAS signal for the sixth scan line with the sixth receiving element 201 positioned in the middle. Furthermore, as shown in the illustration (c) in FIG. 2, the third to eleventh receiving elements 201 are used to obtain a DAS signal for the seventh scan line with the seventh receiving element 201 positioned in the middle. Hence, the DAS signals for the three neighboring scan lines can be generated in a single transmission of the ultrasound waves.

Figure 3:
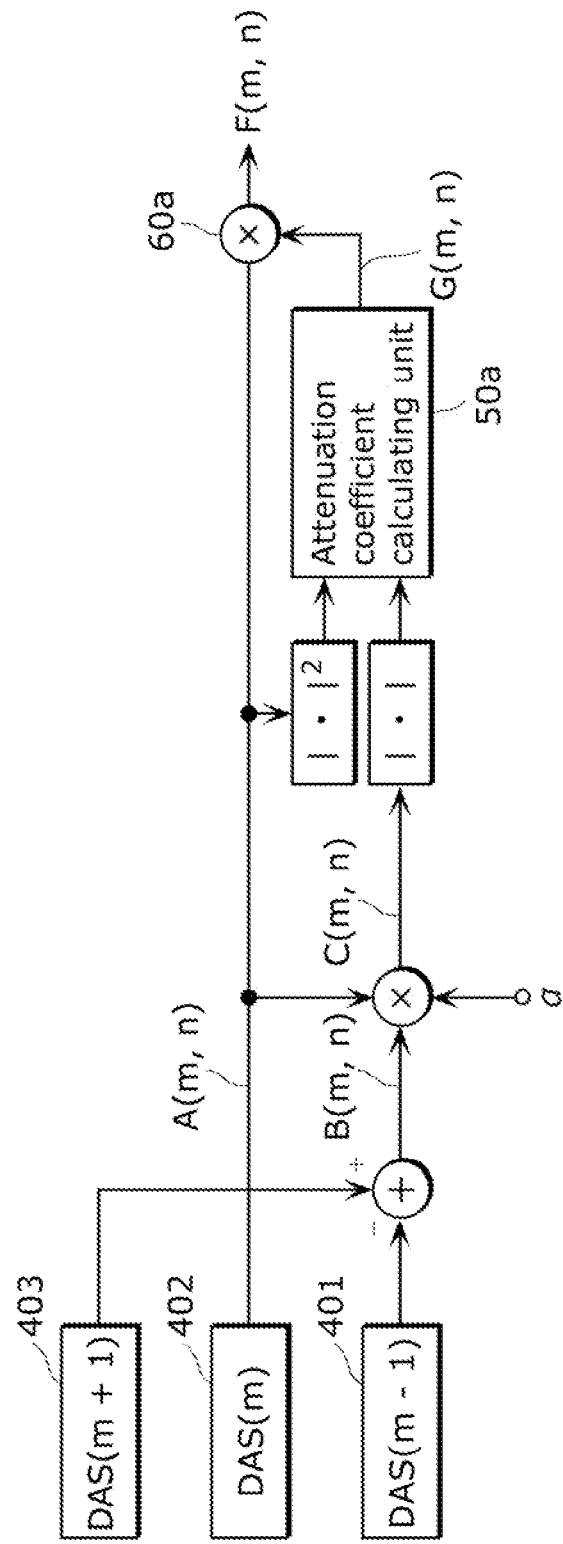
FIG. 3 depicts a block diagram showing how to generate a beamformed signal using three neighboring DAS signals.

Described hereinafter with reference to FIG. 3 is how to improve the resolution of an ultrasound image, using the DAS signals for the three scan lines.

FIG. 3 depicts a block diagram showing how to generate a beamformed signal using three neighboring DAS signals.

In FIG. 3, a DAS signal 401 denoted by DAS (m−1) is, for example, the DAS signal for the fifth scan line as shown in the illustration (a) in FIG. 2. Here, a DAS signal 402 denoted by DAS (m) in FIG. 3 is the DAS signal for the sixth scan line as shown in the illustration (b) in FIG. 2. Similarly, a DAS signal 403 denoted by DAS (m+1) in FIG. 3 is the DAS signal for the seventh scan line as shown in the illustration (C) in FIG. 2.

It is noted that in FIG. 3, signals are denoted in a manner similar to A (m, n). Here, the sign m represents a position of an ultrasound image in a horizontal direction (lateral direction, or the direction in which the receiving elements 201 are aligned). In other words, m represents a scan line number (number of the scan line to be scanned at the end). The sign n represents a position of the ultrasound image in a vertical direction (longitudinal direction, or the depth direction of a target to be observed).

In FIG. 3, the signal A (m, n) is the DAS signal 402 for the th scan line (the m-th scan line positioned in the middle).

A signal B (m, n) is obtained by subtracting the DAS signal 401 for the (m−1)-th scan line from the DAS signal 403 for the (m+1)-th scan line.

A signal C (m, n) is the product of the signal A (m n), the signal B (m, n), and a predetermined coefficient α. In other words, the signal C (m, n) is obtained from the Expression 1 below. It is noted that the predetermined coefficient α is used to adjust narrowness of a beam profile, so that the beam profile of the signal C (m, n) matches that of the signal A (m, n).

[Math. 1]

$$C(m,n) = \alpha \cdot A(m,n) \cdot B(m,n) \qquad \text{Expression 1}$$

An attenuation coefficient calculating unit 50a calculates an amplification factor (attenuation, attenuation coefficient) G (m, n) for reducing a noise component, based on the power signal of the signal A (m, n) and the absolute value of the signal C (m, n). In other words, the attenuation coefficient calculating unit 50a calculates an attenuation coefficient based on Expression 2 below.

[Math. 2]

$$G(m, n) = \frac{|A(m, n)|^2 - |C(m, n)|}{|A(m, n)|^2}$$ Expression 2

It is noted that the signal C (m, n) is the product of the signal A (m, n) and the signal B (m, n), and the dimension of the signal C (m n) is power. In Expression 2, the attenuation coefficient is calculated by matching the dimensions of both the signal A (m, n) and the signal C (m, n) to each other, using the absolute value of the signal C (m, n) and the power of the signal A (m, n).

Finally, the signal A (m, n) is multiplied by the amplification factor G (m, n), and a beamformed signal F (m, n) is generated.

[Math. 3]

$$F(m,n) = A(m,n) \cdot G(m,n)$$ Expression 3

Using the above expressions, the beam profile of the beamformed signal for the m-th scan line is formed narrower.

Figure 4:
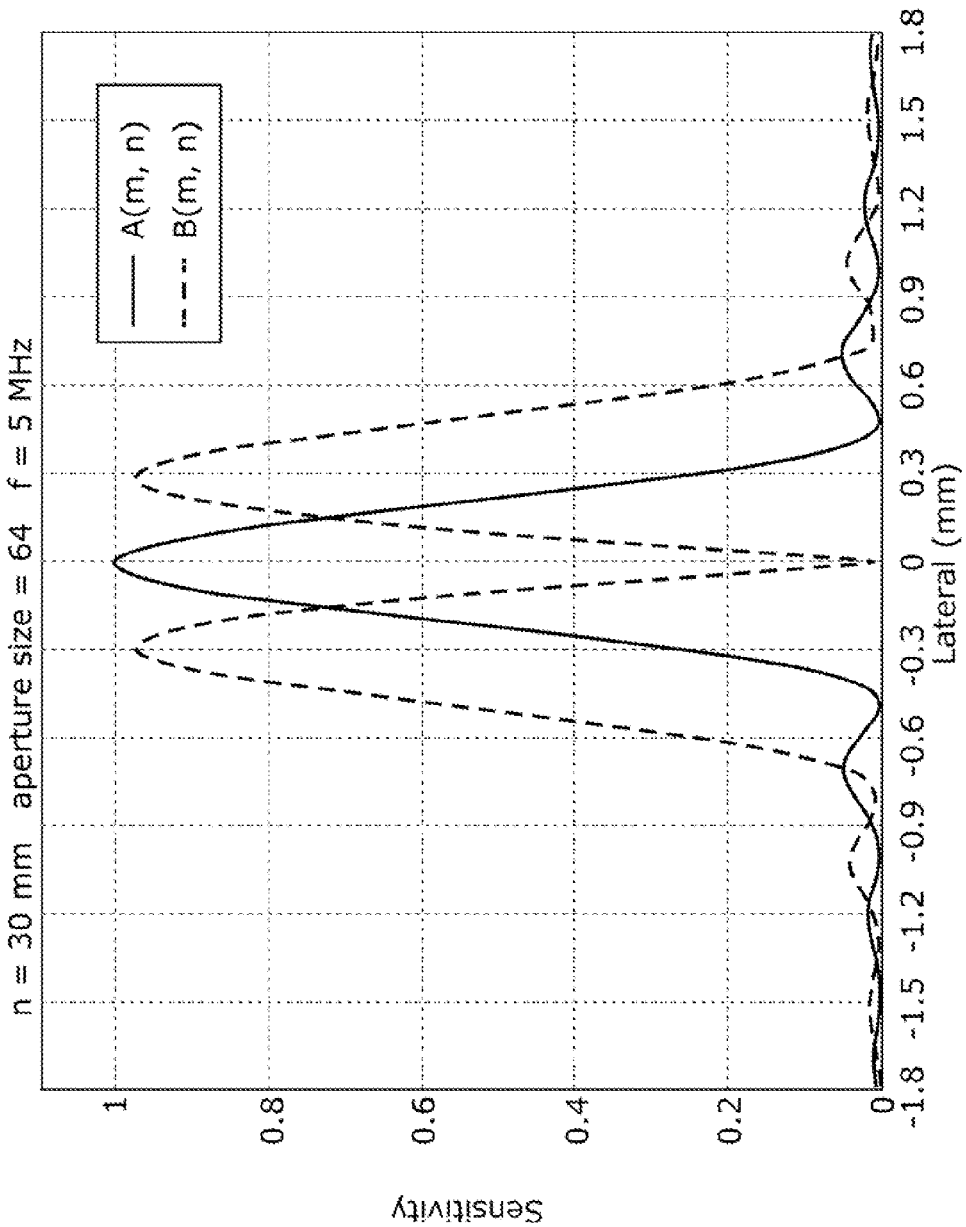
FIG. 4 depicts a first drawing showing the beam profiles of beamformed signals.
Figure 5:
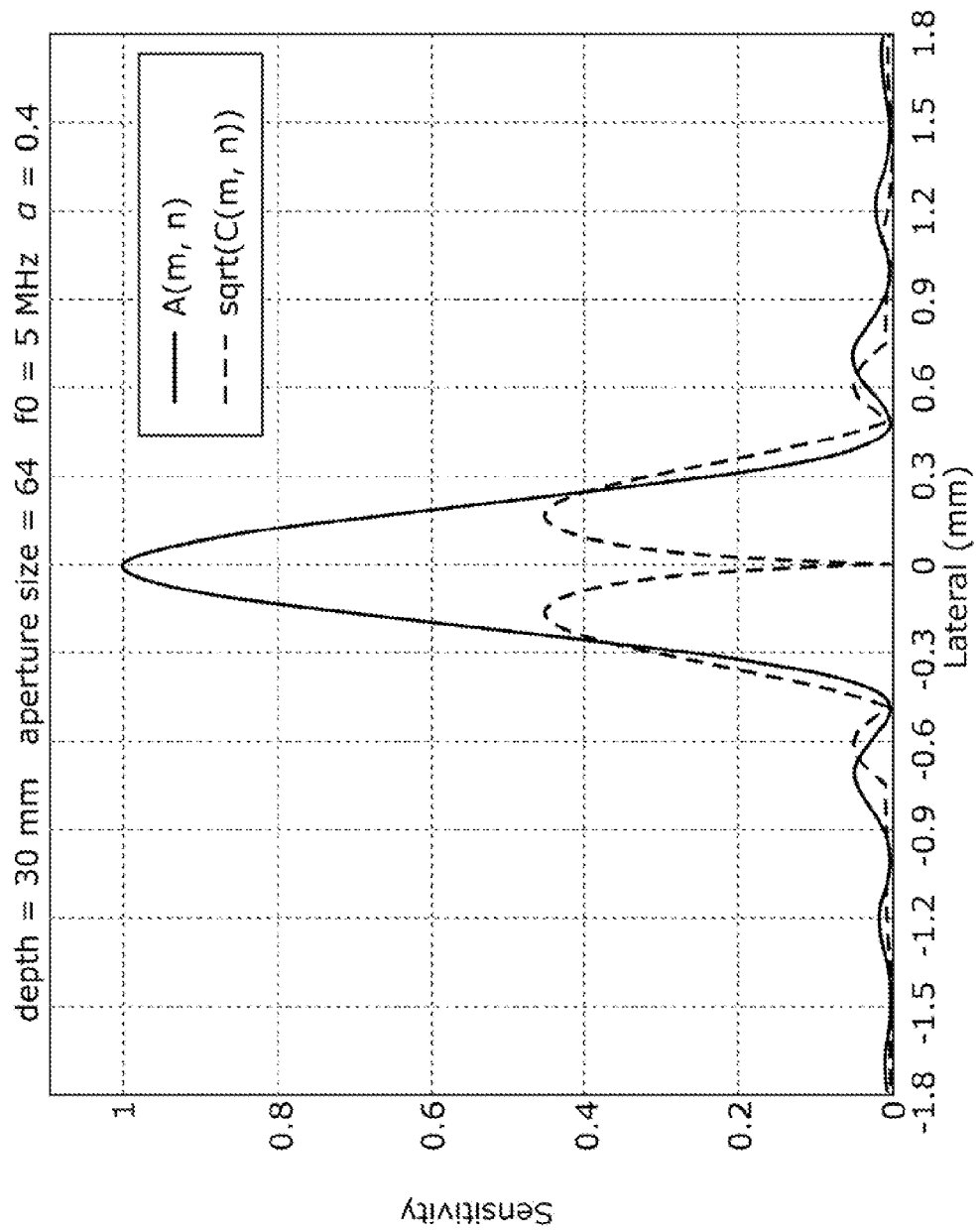
FIG. 5 depicts a second drawing showing the beam profiles of beamformed signals.
Figure 6:
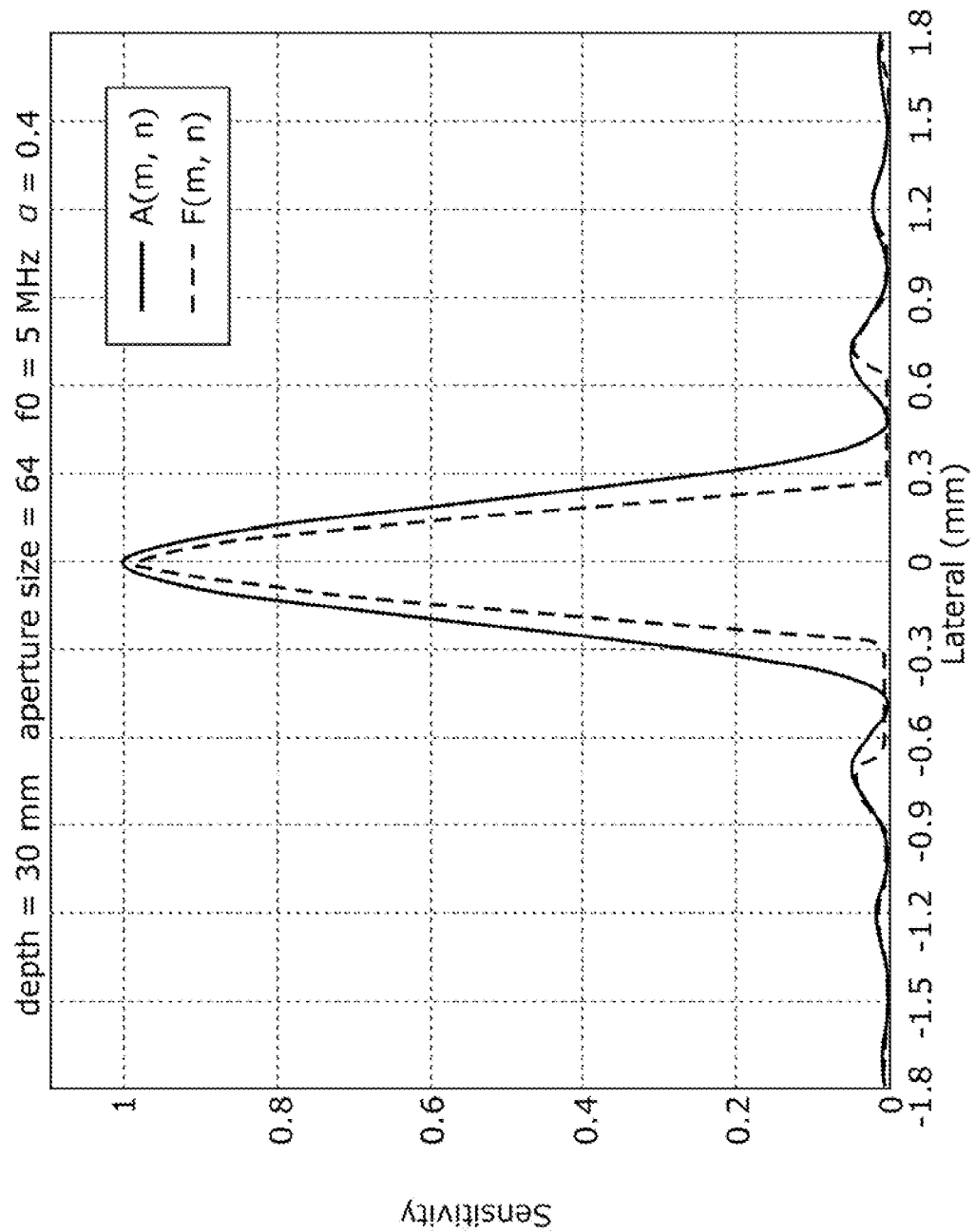
FIG. 6 depicts a second drawing showing the beam profiles of beamformed signals

FIGS. 4 to 6 show the beam profiles of beamformer signals. It is noted that in FIGS. 4 to 6, the beam profiles are calculated under the following conditions: the depth n of 30 mm, the aperture size L of 64 elements, the interval between elements Δd of 0.3 mm, and the transmit frequency f of 5 MHz. Each beam profile shows a level characteristic to sensitivity for the scan line m in a depth n.

The signal A (m, n)—that is the DAS signal 402—has the beam profile illustrated in a solid line in FIG. 4. The signal B (m, n)—that is the difference between the DAS signal 403 and the DAS signal 401—has the beam profile illustrated in a dashed line in FIG. 4.

The signal B (m, n) is obtained as the difference between two DAS signals. One of the DAS signal corresponds to the (m−1)-th scan line and the other one of the DAS signal corresponds to the (m+1)-th scan line, and each of the scan lines is symmetrically positioned distance-wise with respect to the m-th scan line m. Hence, the phase and level match between the two DAS signals on the focal point of the m-th scan line, and a blind spot of sensitivity appears.

The signal B (m, n) is calculated based on the DAS signals for the (m−1)-th scan line and the (m+1)-th scan line, and both the DAS signals have their focal points in a region other than the m-th scan line. Thus, the position where the highest sensitivity is obtained in beam profile is a margin of plus or minus 0.3 mm as shown in FIG. 5—that is as wide as a pitch of an element (width of a scan line). In order to make the signal A (m, n) narrower in beam profile, the maximum sensitivity position of the signal B (m, n) has to be closer to 0 mm. The signal C (m, n) is calculated to obtain such a narrow signal.

In other words, the signal C (m, n) is obtained through matching of the stop band of the signal B (m, n) to the profile of the signal A (m, n). The beam profile of the signal C (m, n) is shown in the dashed line in FIG. 5. In FIG. 5, the beam profile of the sqrt (C(m, n)) is shown as the beam profile of the signal C, such that the signals A and B have the same power.

The amplification factor G (m, n) is obtained with Expression 2, using the signal C (m, n). The obtained amplification factor G (m, n) is multiplied by the signal A (m, n), and the beamformed signal F (m, n) is generated. The beam profile of the beamformed signal F (m, n) is shown in the dashed line in FIG. 6.

As shown in FIG. 6, the beamformed signal F (m, n) generated of the three DAS signals is formed sharper than the beamformed signal A (m, n) conventionally generated of one DAS signal. In other words, the beamformed signal F (m, n) in FIG. 6 is higher in directionality and resolution than the beamformed signal A (m, n).

In the above example, three DAS signals are used to form a sharp beamformed signal. More than three DAS signals would achieve an even further improvement in image quality.

The delay-and-sum operation, however, involves processing many signals. When multiple delay-and-sum operations are executed, a question is how to reduce an amount of the calculations to lower the signal processing load. In particular, it is difficult to execute four or more DAS operations since such operations could pose a significantly heavy signal processing load.

According to an exemplary embodiment disclosed herein, an ultrasonic diagnostic apparatus includes a beamformer which generates beamformed signals, each corresponding to one of scan lines for generating an ultrasound image, from echo signals generated from ultrasound signals bounced off a subject and received by receiving elements. The beamformer includes: a delay-and-sum (DAS) unit configured, for each of frames, to (i) determine one of the scan lines, in a sorting order determined in a given direction, as a target scan line for the frame and select 2k+1 scan lines (k is a positive integer) included in the scan lines and aligned in a row with the target scan line positioned in a middle, and (ii) perform a DAS operation on each of the echo signals to calculate a first DAS signal which is a DAS signal for the target scan line and second DAS signals which are DAS signals each for one of the selected 2k+1 scan lines other than the target scan line; a first reference beam generating unit which generates a first reference beam from the first DAS signal and the second DAS signals all of which are calculated in an N-th frame of the frames; a second reference beam generating unit which generates a second reference beam from (i) one of the second DAS signals which is calculated in an (N−1)-th frame of the frames immediately preceding the N-th frame and is generated for one of the scan lines which has an earliest number in the sorting order, (ii) the first DAS signal which is calculated in the N-th frame and (iii) another one of the second DAS signals which is calculated in an (N+1)-th frame of the frames immediately succeeding the N-th frame and is generated for another one of the scan lines which has a latest number in the sorting order; an attenuation coefficient calculating unit which calculates, based on the first reference beam and the second reference beam, an attenuation coefficient for forming narrower a profile of the first DAS signal calculated in the N-th frame; and a beamforming unit which generates and provide a beamformed signal included in the beamformed signals and generated for the target scan line in the N-th frame, by multiplying the first DAS signal calculated in the N-th frame by the attenuation coefficient.

The above features make it possible to reduce the number of DAS operations to be simultaneously executed to decrease an amount of calculations, as well as improve the resolution of an image.

For each of the frames, the DAS unit may select three scan lines included in the scan lines and aligned in a row with the target scan line positioned in a middle of the selected three scan lines, and calculate the first DAS signal and the second DAS signals, the second DAS signals each being generated for one of two scan lines included in the three scan lines, and the two scan lines each neighboring the target scan line. The first reference beam generating unit may generate the first reference beam from the first DAS signal and two second DAS signals all of which are calculated in the N-th frame, the two second DAS signals being the second DAS signals each generated for one of the two scan lines.

The above feature makes it possible to generate an image whose resolution is as high as one generated with five DAS operations even though only three DAS operations are executed for one frame.

In the case where the target scan line in the N-th frame is either an endmost scan line among the scan lines or a second scan line from the endmost scan line among the scan lines, the beamforming unit may provide the first DAS signal calculated in the N-th frame as the beamformed signal for the target scan line in the N-th frame.

The above feature makes it possible to appropriately generate a beamformed signal for the endmost scan line.

In the case where the target scan line in the N-th frame is a second scan line from an endmost scan line among the scan lines, the attenuation coefficient calculating unit may calculate the attenuation coefficient determined based only on the first reference beam of the first reference beam and the second reference beam, and the beamforming unit may generate and provide the beamformed signal for the target scan line in the N-th frame, by multiplying the first DAS signal calculated in the N-th frame by the attenuation coefficient determined based only on the first reference beam.

The above feature makes it possible to appropriately generate a beamformed signal for the second scan line from the endmost scan line.

The first reference beam generating unit may generate the first reference beam by multiplying the first DAS signal calculated in the N-th frame by a difference between the two second DAS signals calculated in the N-th frame, and the second reference beam generating unit may generate the second reference beam by multiplying the first DAS signal calculated in the N-th frame by a difference between the one second DAS signal and the other second DAS signal, the one second DAS signal being calculated in the (N−1)-th frame and generated for the one scan line having the earliest number in the sorting order and the other second DAS signal being calculated in the (N+1)-th frame and generated for the other scan line having the latest number in the sorting order.

The first reference beam generating unit may generate the first reference beam by multiplying the first DAS signal calculated in the N-th frame by a difference between the two second DAS signals calculated in the N-th frame, and the second reference beam generating unit may generate the second reference beam by multiplying the first DAS signal calculated in the N-th frame by a difference between the one second DAS signal and the other second DAS signal, the one second DAS signal being calculated in the (N−1)-th frame and generated for the one scan line having the earliest number in the sorting order and the other second DAS signal being calculated in the (N+1)-th frame and generated for the other scan line having the latest number in the sorting order.

The attenuation coefficient calculating unit may calculate G which is the attenuation coefficient, using after-described Expression 5, where A is the first DAS signal calculated in the N-th frame, C is the first reference beam, and E is the second reference beam.

The attenuation coefficient calculating unit may, based on a distance between positions of the receiving elements and a point where the ultrasound signals start to bounce off, selectively execute (i) calculation of the attenuation coefficient based on both the first reference beam and the second reference beam, (ii) calculation of the attenuation coefficient based only on the first reference beam of the first reference beam and the second reference beam, and (iii) calculation of the attenuation coefficient to be 1.

The above features make it possible to execute control, directed to a target scan line in which a beam profile tends to be wide—that is a target scan line whose depth is great—, to increase the number of DAS signals to be used for the calculation of an attenuation coefficient. In other words, the above features make it possible to improve the resolution of an ultrasound image, depending on the depth.

The attenuation coefficient calculating unit may, based on a number of the target scan line in the sorting order in the N-th frame, selectively execute (i) calculation of the attenuation coefficient based on both the first reference beam and the second reference beam, (ii) calculation of the attenuation coefficient based only on the first reference beam of the first reference beam and the second reference beam, and (iii) calculation of the attenuation coefficient to be 1.

The above feature makes it possible to change the number of the DAS signals to be used for the calculation of an attenuation coefficient depending on positions of a target scan line, such as the endmost of an image where the number of the DAS signals is limited and the middle of an image where there is no limitation on the number of the DAS signals.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Hereinafter, certain exemplary embodiments are described in greater detail with reference to the accompanying Drawings. Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the scope of the appended Claims and their equivalents. Therefore, among the structural elements in the following exemplary embodiments, structural elements not recited in any one of the independent claims are described as arbitrary structural elements. In addition, the same constituent elements have the same reference numerals, and the details thereof may be omitted.

Embodiment 1

Described first is an overall structure of an ultrasonic diagnostic apparatus according to Embodiment 1.

Figure 7:
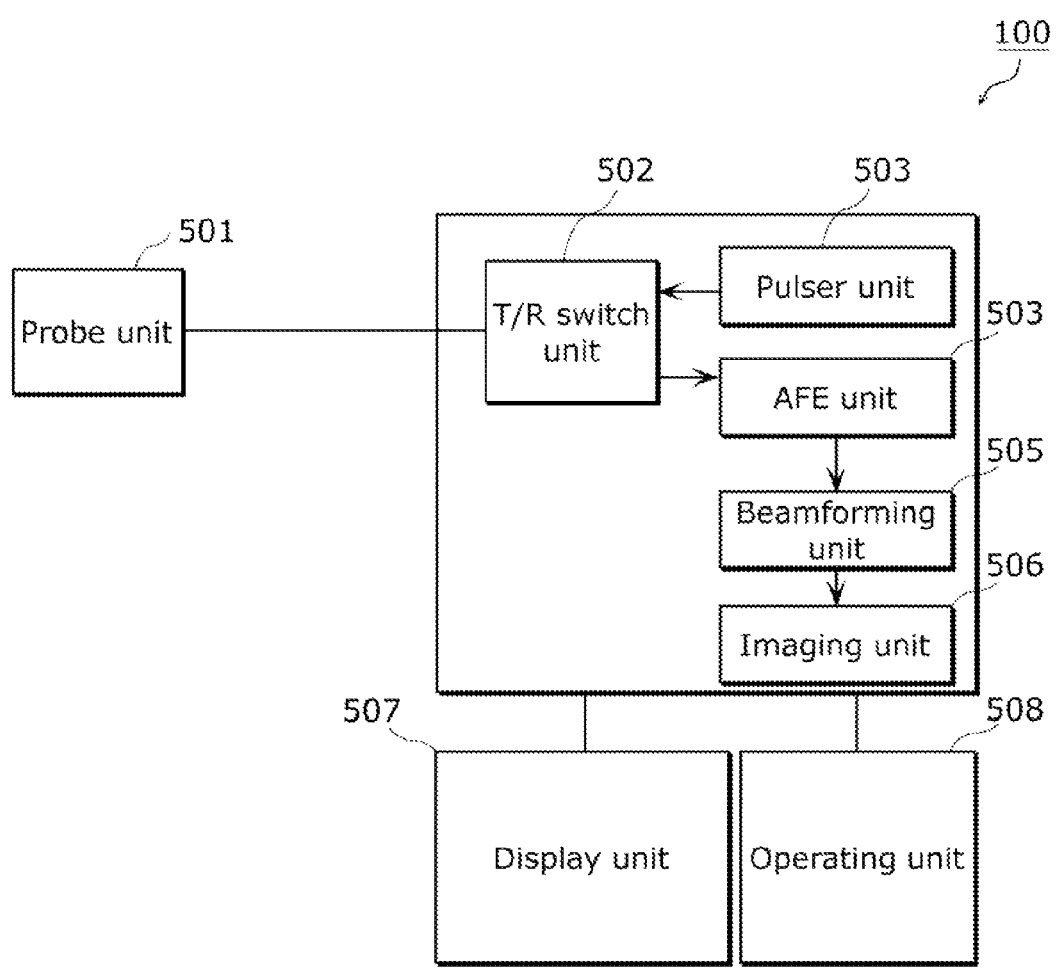
FIG. 7 depicts a block diagram showing a structure of an ultrasonic diagnostic apparatus according to Embodiment 1.

FIG. 7 depicts a block diagram showing a structure of the ultrasonic diagnostic apparatus according to Embodiment 1.

An ultrasonic diagnostic apparatus 100 includes: a probe unit 501, a transmission/reception (T/R) switch unit 502, a puller unit 503, an AFE (analogue front end) unit 504, a beamforming unit 505 (beamformer), an imaging unit 506, a display unit 507, and an operating unit 508.

The probe unit 501 transmits ultrasound waves to a sample (also referred to as subject. A body, for example), and receives the ultrasound waves bounced off the sample to generate echo signals.

The T/R switch unit 502 electrically switches between a transmission signal to be transmitted to the probe unit 501 and an echo signal to be received from the probe unit 501 in view of circuit protection.

The puller unit 503 generates an electric signal which prompts the transmission of the ultrasound waves.

The AFE unit 504 receives the echo signals generated by the probe unit 501 from reflected waves—in other words, the reflected waves are the ultrasound waves transmitted by the probe unit 501 and reflected off the sample. The AFE unit 504 then amplifies the echo signals and performs analogue-digital conversion on the echo signals to convert the echo signals into a sequence of digital signals. The AFE unit 504 operates as so-called an analogue front end.

The beamforming unit 505 performs beamforming by array signal processing on the digital signal sequence generated by the AFE unit 504. The beamforming corresponds to focusing processing performed on a region to be visible.

The imaging unit 506 generates a display image (ultrasound image) from the signals obtained by the beamforming unit 505.

The display unit 507 displays the display image generated by the imaging unit 506. For example, the display unit 507 may include a liquid crystal display and an organic electro luminescence (EL) display.

The operating unit 508 operates the above functional blocks as well as controls the processing performed by each of the functional blocks. Furthermore, the operating unit 508 may receive operations by a user and perform the control and operations.

In particular, a feature of the present disclosure is the beamforming unit 505 for generating a beam signal used for generating an ultrasound image through calculation of echo signals of ultrasound waves. It is noted that the constituent elements other than the features of the present disclosure may be substituted in ones for a conventional ultrasonic diagnostic apparatus. Hence, the beamforming unit 505 may be introduced in the present disclosure instead of a beamforming unit for a conventional ultrasonic diagnostic apparatus.

It is noted that the ultrasonic diagnostic apparatus 100 shall not be limited to the ultrasonic diagnostic apparatus shown in FIG. 7. For example, the T/R switch unit 502 may be omitted in the case where different elements are used for transmission and for reception. Furthermore, the probe unit 501 may include the pulser unit 503. The probe unit 501 may include the pulser unit 503 and the AFE unit 504. In addition, the probe unit 501 may include all the other functional blocks.

Figure 8:
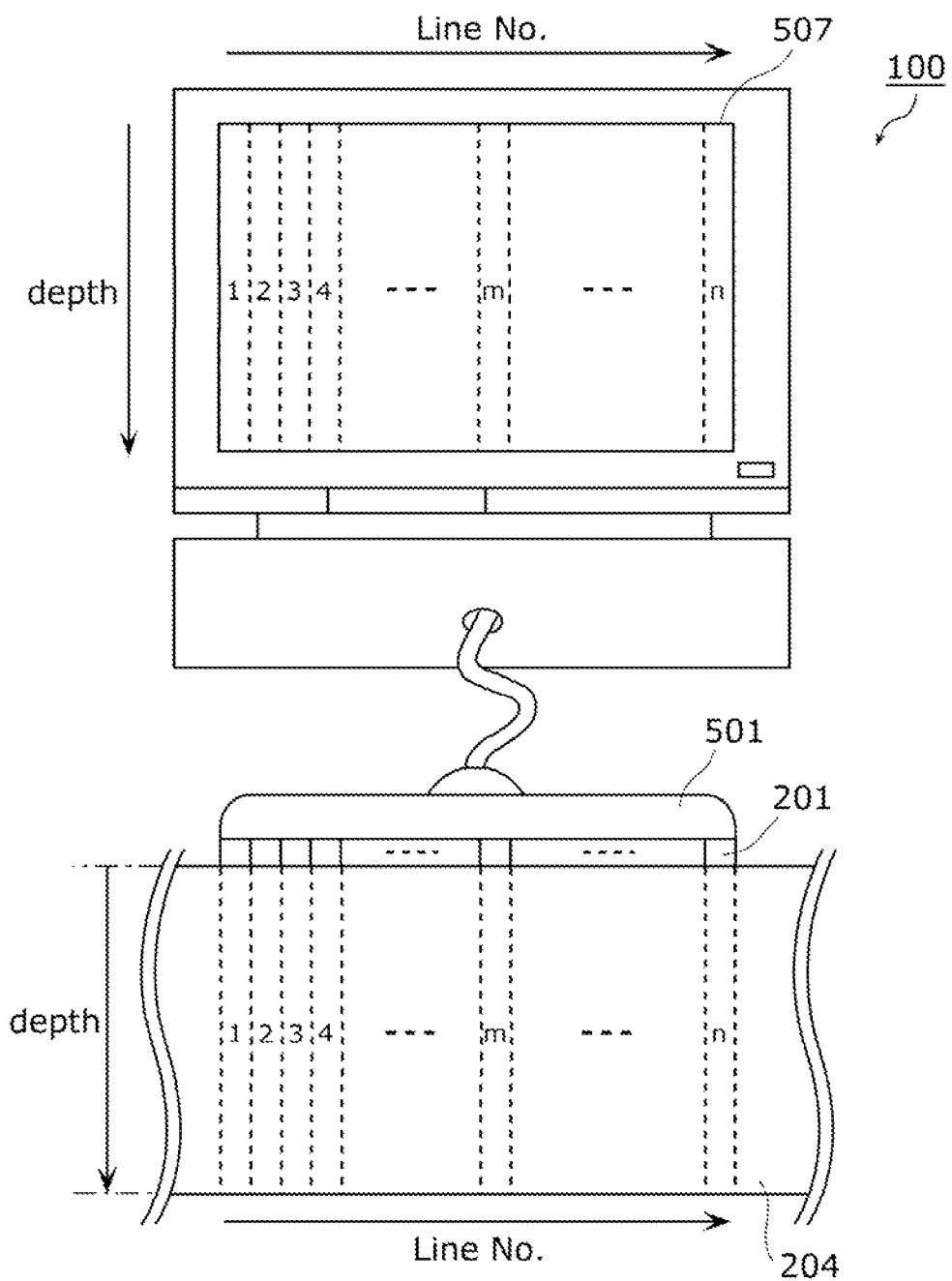
FIG. 8 schematically illustrates a relationship between receiving elements and scan lines according to Embodiment 1

The relationship between multiple receiving elements 201 and scan lines in the probe unit 501 in Embodiment 1 is illustrated in FIG. 8.

FIG. 8 schematically illustrates a relationship between receiving elements and scan lines according to Embodiment 1. It is noted that in FIG. 8 the illustration on the top shows an appearance of the display unit 507, and the illustration on the bottom shows a cross-sectional view when the probe, unit 501 is applied to a subject 204.

As shown in FIG. 8, the subject 204 is partitioned into n scan lines (regions) each corresponding to one of the n receiving elements 201 arranged in a row. In addition, as shown in FIG. 8, the depth direction is defined to be the one approximately vertical to the probe unit 501's surface applied to the subject 204.

Here, as shown in FIG. 8, the display unit 507 of the ultrasonic diagnostic apparatus 100 displays, based on a beamformed signal generated for each frame, one scan line for each frame. In other words, in Embodiment 1, a frame is a unit of time for generating one scan line. In the description below, each ultrasound image for one scan line is generated in order (in the order of 1, 2, . . . n) from the end of the ultrasound image along with frame progress.

The transmission of the ultrasound waves is executed by a not-shown transmitting unit included in the probe unit 501. The transmitting unit transmits (emits) ultrasound wave toward the subject from positions each corresponding one of the receiving elements 201. The receiving elements 201 receive bounced signals and generate echo signals.

It is noted that when the display unit 507 actually displays an ultrasound image, the n scan lines are not sufficient in the number of scan lines for display. Here, for displaying the ultrasound image, the number of scan lines may be increased to 2n by, for example, interpolation processing.

Described next is the beamforming unit 505—that is a feature of the ultrasonic diagnostic apparatus 100—in a comparison with a conventional beamforming unit.

Described first is the conventional beamforming unit.

Figure 9:
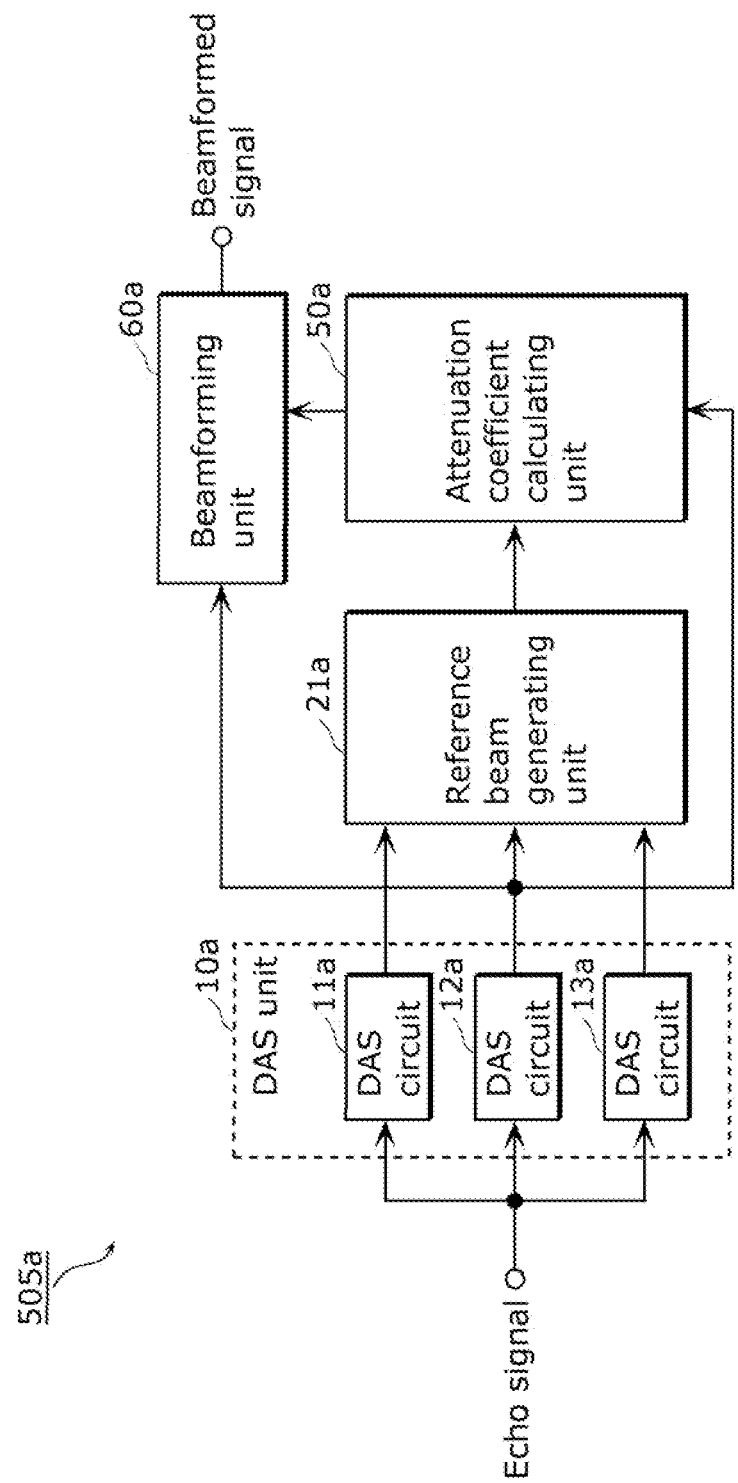
FIG. 9 depicts a first block diagram showing a structure of a conventional beamforming unit.

FIG. 9 depicts a structure of the conventional beamforming unit.

A beamforming unit 505a shown in FIG. 9 includes a DAS unit 10a including three DAS circuits 11a to 13a, a reference beam generating unit 21a, the attenuation coefficient calculating unit 50a, and a beamforming unit 60a.

The DAS unit 10a obtains three DAS signals from an echo signal generated when the receiving elements 201 receives ultrasound signals bounced off the subject 204. In the three DAS signals, the DAS signal positioned in the middle is at a transmission position (position of any one of the receiving elements 201) where the ultrasound waves are transmitted for generating the echo signal.

Specifically, when the scan line corresponding to the transmission position is deemed as a target scan line, a DAS signal for the target scan line is calculated (generated) by the DAS circuit 12a. The DAS signals on the both sides of the target scan line are generated by the DAS circuits 11a and 13a. The DAS signals generated by the DAS circuits 11a to 13a are provided to the reference beam generating unit 21a.

As detailed with FIG. 3, the reference beam generating unit 21a generates the signal C using each of the DAS signals generated by the DAS circuits 11a to 13a. The signal C is obtained through matching of the stop band of the signal B to the profile of the signal A. The signal C is an output from the reference beam generating unit 21a. It is noted that the reference beam generating unit 21a may generate the reference beam by a technique other than the one shown in FIG. 3.

According to Expression 2, the attenuation coefficient calculating unit 50a calculates an attenuation coefficient.

The beamforming unit 60a generates a beamformed signal for the target scan line by multiplying the attenuation coefficient calculated by the attenuation coefficient calculating unit 50a with the DAS signal, for the target scan line, provided from the DAS circuit 12a.

The beamforming unit 505a can form a beamformed signal sharp, using the three DAS signals (see FIG. 6). Here, more than three DAS signals, for example five DAS signals, allow a beamforming unit to generate an image having even higher quality.

Figure 10:
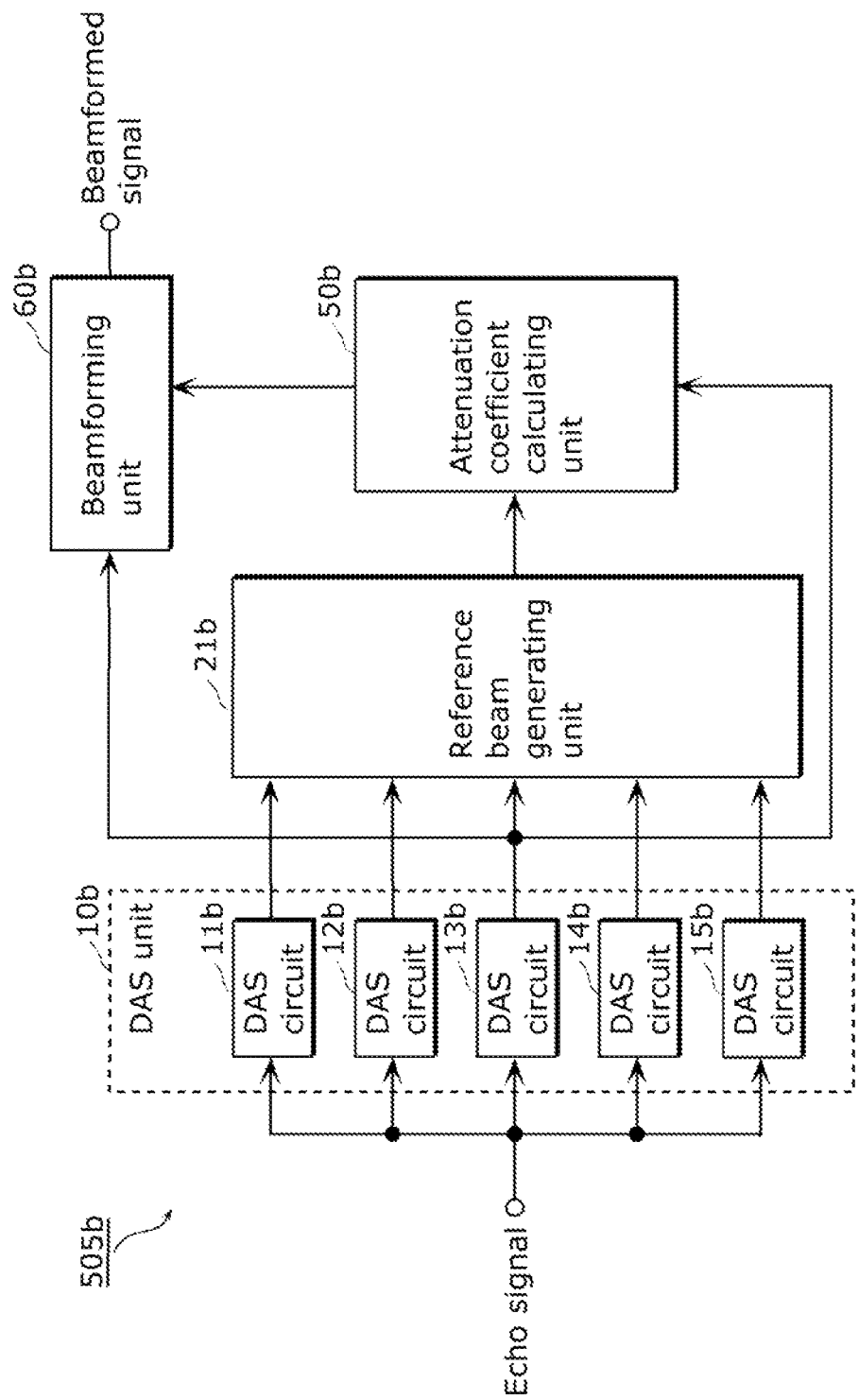
FIG. 10 depicts a first block diagram showing a structure of a conventional beamforming unit.

FIG. 10 depicts a block diagram showing a structure of a conventional beamforming unit for calculating five DAS signals.

A beamforming unit 505b shown in FIG. 10 includes a DAS unit 10b including five DAS circuits 11b to 15b, a reference beam generating unit 21b, an attenuation coefficient calculating unit 50b, and a beamforming unit 60b.

The DAS unit 10b obtains five DAS signals from an echo signal, using the DAS circuits 11b to 15b. The calculated five DAS signals are provided to the reference beam generating unit 21b. The succeeding processing is almost similar to the one performed by the beamforming unit 505a.

The DAS operations, however, inevitably require a significantly large amount of calculations. This is because the DAS operations handle significantly large amount of data to generate DAS signals from an echo signal. Hence, in reality, it is difficult to simultaneously calculate four or more DAS signals.

The beamforming unit 505 according to Embodiment 1 then generates the beamformed signal for a target scan line, using a DAS signal calculated in the current frame, a DAS signal calculated in one frame before the current frame, and a DAS signal calculated in one frame after the current frame.

Consequently, the generated beamformed signal is formed narrow using five DAS signals even though only three DAS signals are calculated in one frame.

Figure 11:
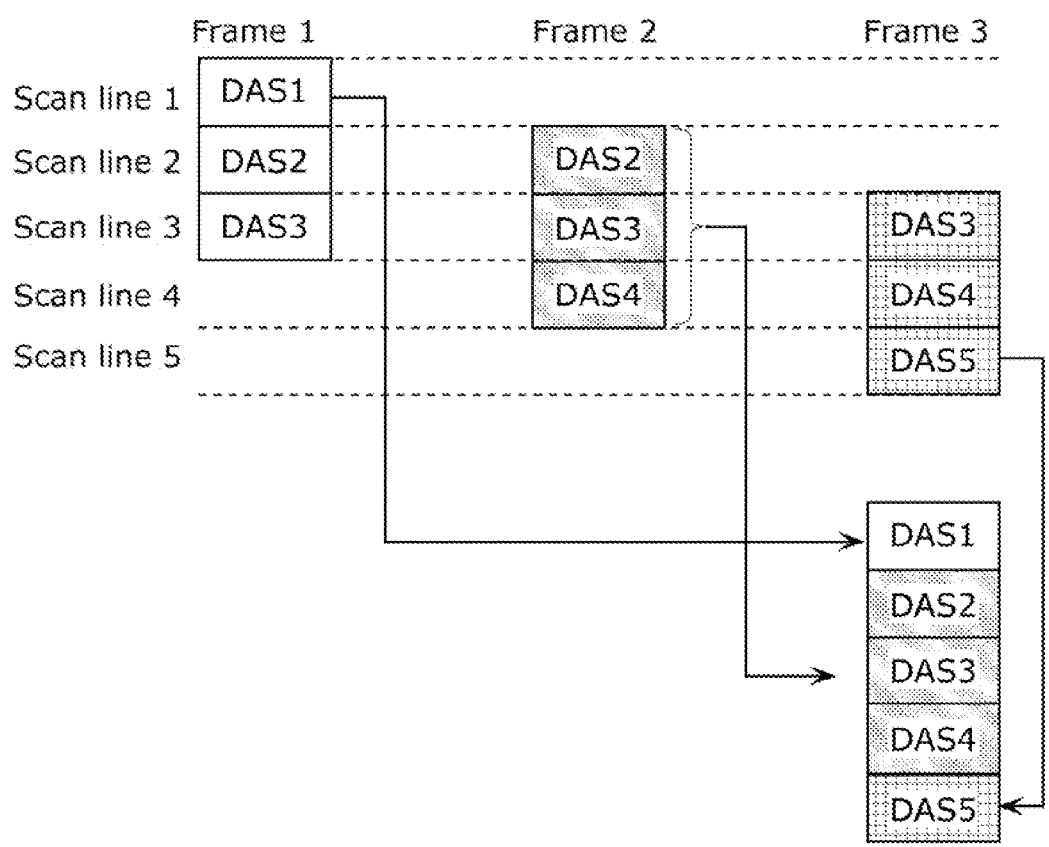
FIG. 11 briefly shows how a beamforming unit according to Embodiment 1 generates a beamformed signal.

FIG. 11 briefly shows how the beamforming unit 505 according to Embodiment 1 generates a beamformed signal.

In FIG. 11, the processing is executed in the order of frames 1 to 3. In the frame 1, a scan line 2 is the target scan line (scan line positioned in the middle). In the frame 2, a scan line 3 is the target scan line. In the frame 3, a scan line 4 is the target scan line.

In the frame 1 (time of the frame 1) on the far left in FIG. 11, an ultrasound wave is transmitted at a transmission position corresponding to the scan line 2 (position of a receiving element 201 corresponding to the scan line 2). In the frame 1, a DAS unit calculates the following DAS signals from an echo signal obtained through the transmission: a DAS 2 which is a DAS signal for the scan line 2, a DAS 1 which is a DAS signal for the scan line 1 neighboring the scan line 2, and a DAS 3 which is a DAS signal for the scan line 3 adjacent to the scan line 2.

In the frame 2 following the frame 1 and shown in the middle in FIG. 11, an ultrasound wave is transmitted at a transmission position corresponding to the scan line 3. In the frame 2, the DAS unit calculates the following DAS signals from an echo signal obtained through the transmission: the DAS 3 which is a DAS signal for the scan line 3, the DAS 2 which is a DAS signal for the scan line 2, and a DAS 4 which is a DAS signal for a scan line 4.

In the frame 3 following the frame 2 and shown in the right of FIG. 11, an ultrasound wave is transmitted at a transmission position corresponding to the scan line 4. In the frame 3, the DAS unit calculates the following DAS signals from an echo signal obtained through the transmission: the DAS 4 which is a DAS signal for the scan line 4, the DAS 3 which is a DAS signal for the scan line 3, and a DAS 5 which is a DAS signal for a scan line 5.

DAS data calculated in the frames 1 and 2 is stored in a buffer. Using the DAS 1 calculated in the frame 1, the DAS 2 to DAS 4 calculated in the frame 2, and the DAS 5 calculated in the frame 3, a beamformed signal for the scan line 3 is generated.

Utilizing the above technique, the beamforming unit 505 according to Embodiment 1 can generate, after the frame 3, a beamformed signal for the scan line 3—that is the target scan line in the frame 2—from DAS signals for five scan lines aligned in a row.

According to the structure of the beamforming unit 505, three DAS signals are calculated per frame; however, the structure makes it possible to generate an image whose resolution is as high as the resolution to be obtained based on five DAS signals per frame.

Described hereinafter is a structure and operations of the beamforming unit 505 according to Embodiment 1

Figure 12:
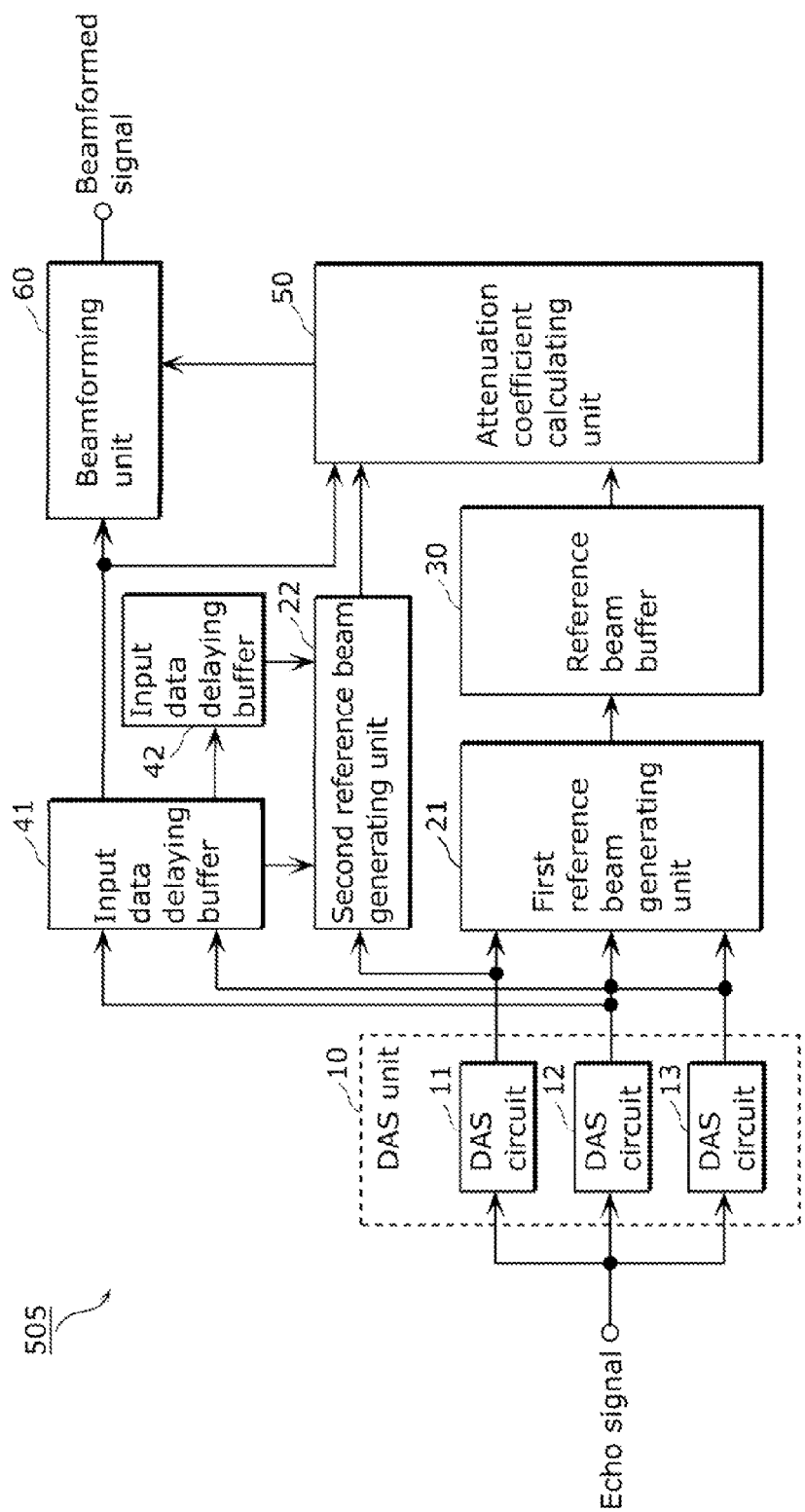
FIG. 12 depicts a block diagram showing a structure of the beamforming unit according to Embodiment 1.

FIG. 12 depicts a block diagram showing the structure of the beamforming unit 505 according to Embodiment 1.

Figure 13:
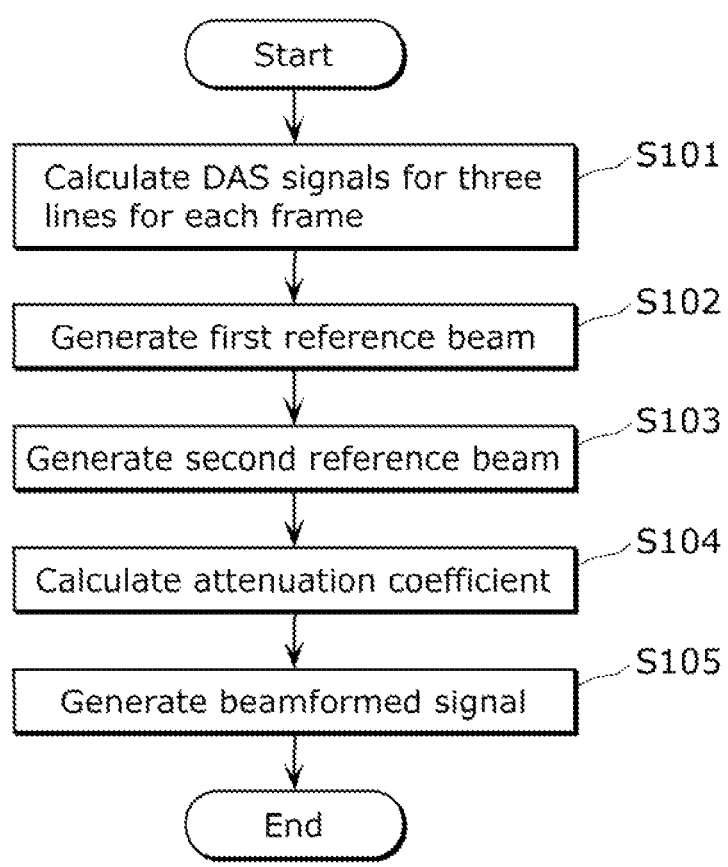
FIG. 13 depicts a flowchart showing operations of the beamforming unit according to Embodiment 1.

FIG. 13 depicts a flowchart showing the operations of the beamforming unit 505 according to Embodiment 1.

As shown in FIG. 12, the beamforming unit 505 according to Embodiment 1 includes a DAS unit 10 including three DAS circuits 11 to 13, a first reference beam generating unit 21, a second reference beam generating unit 22, an attenuation coefficient calculating unit 50, a beamforming unit 60, a reference beam buffer 30, and input data delaying buffers 41 and 42.

As described above, the beamforming unit 505 generates beamformed signals, each corresponding to one of the scan lines aligned in order for generating an ultrasound image, from echo signals generated from ultrasound signals bounced off the subject 204 and received by the receiving elements 201.

The DAS unit 10 calculates three DAS signals from n echo signal for each frame (S101 in FIG. 13).

Specifically, for each frame, the DAS unit 10 first determines, in the sorting order of the scan lines, one of the scan lines as the target scan line for the frame, and selects three scan lines aligned in a row with the target scan line positioned in the middle of the three scan lines.

As an example of the frame 1 in FIG. 11, the DAS unit 10 determines the scan line 2 as the target scan line, and selects three scan lines 1 to 3 aligned in a row with the scan line 2 in the middle. In frame 2, the DAS unit 10 determines the scan line 3 as the target scan line, and selects three scan lines 2 to 4 aligned in a row with the scan line 3 in the middle.

Moreover, for each frame, the DAS unit 10 performs a DAS operation on each of echo signals to calculate a first DAS signal which is a DAS signal for the target scan line and second DAS signals which are DAS signals for two of the three scan lines other than the target scan line.

As an example of the frame 1 in FIG. 11, the DAS unit 10 calculates the first DAS signal which is a DAS signal for the scan line 2 and the second DAS signals which are DAS signals each for one of two scan lines—the scan lines 1 and 3.

The DAS circuit 12 calculates the first DAS signal. The DAS circuit 11 calculates a DAS signal for one of the two scan lines neighboring the target scan line, the one scan line having the later number of the two scan lines in a sorting order. The DAS circuit 13 calculates a DAS signal for another one of the two scan lines neighboring the target scan line, the other one scan line having the earlier number of the two scan lines in the sorting order.

It is noted that the first DAS signal is stored in the input data delaying buffer 41, and available in the immediately subsequent frame. Hence, in the current frame, the second reference beam generating unit 22 can use the first DAS signal calculated in the immediately preceding frame.

Similarly, one of the second DAS signals which is for the scan line having the earlier number of the scan lines in the sorting order (the second DAS signal calculated by the DAS circuit 13) is stored in the input data delaying buffer 41 and then in the input data delaying buffer 42. Hence, in the current frame, the second reference beam generating unit 22 can use the second DAS signal calculated in the frame two frames before.

As an example of the frame 3 in FIG. 11, the input data delaying buffer 42 stores the signal (the DAS 1) calculated by the DAS circuit 13 in a frame two frames before—that is, the frame 1. Similarly, the input data delaying buffer 41 stores the signals (the DAS 2 and the DAS 3) calculated by the DAS circuits 12 and 13 in the immediately preceding frame—that is, the frame 2.

Moreover, the first DAS signal and the second DAS signals calculated by the DAS unit 10 (the DAS circuits 11 to 13) are provided to the first reference beam generating unit 21, and the first reference beam generating unit 21 generates a first reference beam.

The first reference beam generating unit 21 generates the first reference beam from the first DAS signal and the two second DAS signals all of which are calculated in the N-th frame (S102 in FIG. 13).

In the above example of FIG. 11, the first reference beam generating unit 21 generates the first reference beam, using the first DAS signal (the DAS 3) which is a DAS signal for the scan line 3 calculated in the frame 2 and the second DAS signals (the DAS 2 and the DAS 4) which are DAS signals each for one of the scan lines 2 and 4 calculated in the frame 2. Details of how to generate the first reference beam shall be described later.

It is noted that the first reference beam generated by the first reference beam generating unit 21 is stored in the reference beam buffer 30 and then provided to the attenuation coefficient calculating unit 50. Such a feature allows the attenuation coefficient calculating unit 50 to use in the current frame the first reference beam generated in the immediately preceding frame.

The second reference beam generating unit 22 generates a second reference beam from (i) one of the second DAS signals which is calculated in the (N−1)-th frame immediately preceding the N-th frame, and is generated for one of the scan lines which has an earliest number in the sorting order, (ii) the first DAS signal which is calculated in the N-th frame, and (iii) another one of the second DAS signals which is calculated in an (N+1)-th frame of the frames immediately succeeding the N-th frame and is generated for another one of the scan lines which has a latest number in the sorting order (S103 in FIG. 13). Details of how to generate the second reference beams shall be described later.

In the above example of FIG. 11, the second reference beam generating unit 22 generates the second reference beam, using one second DAS signal (the DAS 1) for the scan line 1 calculated in the frame 1, the first DAS signal (the DAS 3) for the scan line 3 calculated in the frame 2, and another second DAS signal (a DAS 5) for the scan line 5 calculated in the frame 3.

Here, the second DAS signal for the scan line 1 calculated in the frame 1 is one of the second DAS signals calculated in the (N−1)-th frame and having the scan line with the earliest number in the sorting order. The first DAS signal for the scan line 3 calculated in the frame 2 is the one calculated in the N-th frame. The second DAS signal for the scan line 5 calculated in the frame 3 is one of the second DAS signals calculated in the (N+1)-th frame and having the scan line with the latest number in the sorting order.

The attenuation coefficient calculating unit 50 calculates an attenuation coefficient (S104 in FIG. 13). The attenuation coefficient is determined based on the first and the second reference beams and used for forming narrower the profile of the first DAS signal calculated in the N-th frame. The details of how to calculate the attenuation coefficient shall be described later.

The beamforming unit 60 generates and provides a beamformed signal for the target scan line in the N-th frame, by multiplying the first DAS signal calculated in the N-th frame by the attenuation coefficient calculated by the attenuation coefficient calculating unit 50 (S105 in FIG. 13).

Thanks to the above features, the beamforming unit 505 can generate a beamformed signal using DAS signals for five scan lines while the DAS signals to be calculated are still for three scan lines for each frame.

It is noted that the beamforming unit 505 executes the processing in Step S102 in the N-th frame and the processing in Steps S103 to S105 in the (N+1)-th frame; however, the processing timing shall not be defined as it is. The processing in Step S102 may be executed in a frame following the N-th frame. The processing in Steps S103 to S105 may be executed in a frame following the (N+1)-th frame.

Described next in detail are how to generate the first and the second reference beams and how to calculate an attenuation coefficient (how to generate a beamformed signal) based on the first and the second reference beams.

Figure 14:
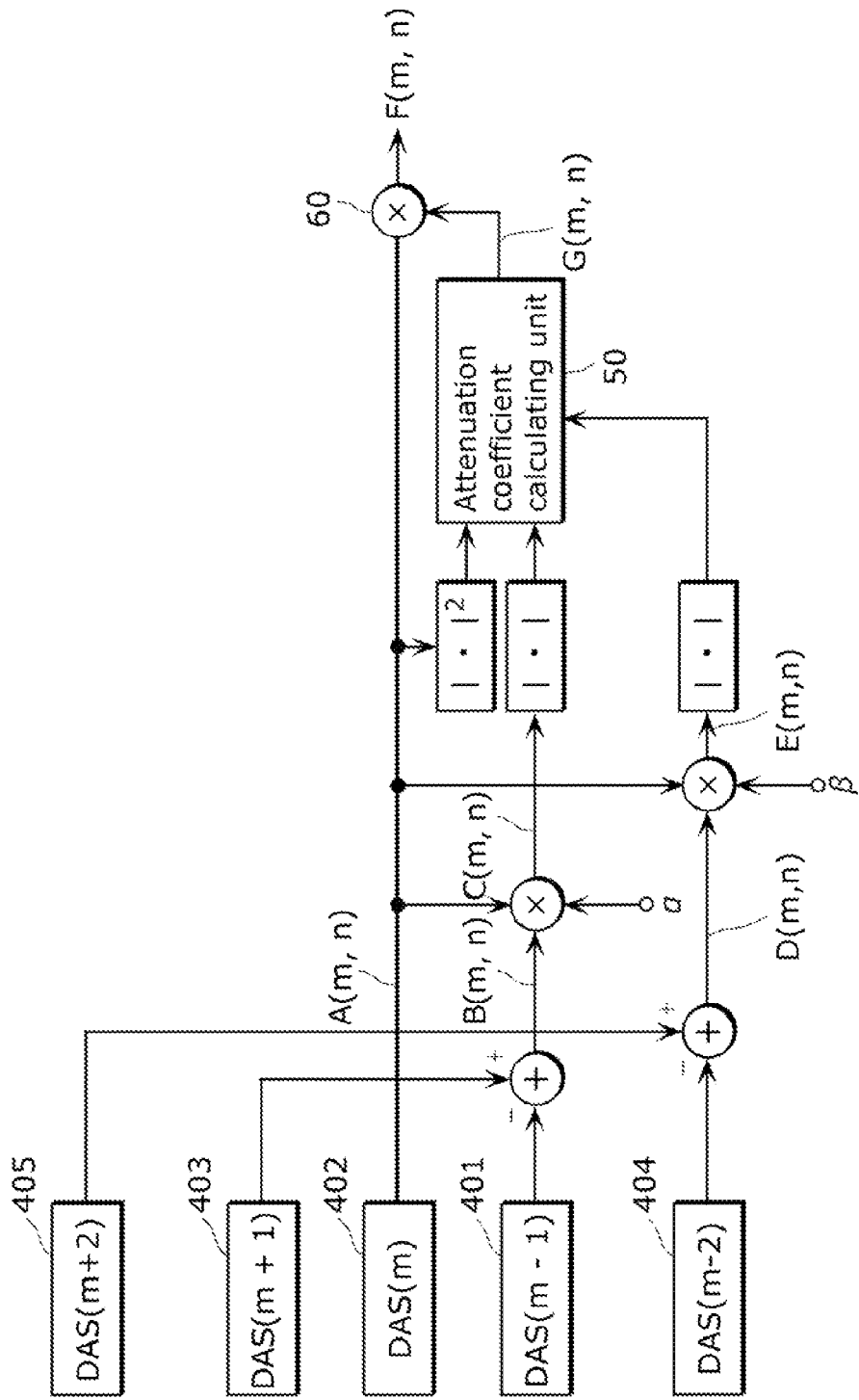
FIG. 14 depicts a block diagram showing how a beamforming unit according to Embodiment 1 generates a beamformed signal.

FIG. 14 depicts a block diagram showing a structure of the beamforming unit 505 according to Embodiment 1. It is noted that in FIG. 14, the DAS signal denoted as DAS(m) is the DAS signal for the m-th scan line.

The first reference beam generating unit 21 generates the first reference beam from the following three DAS signals calculated in the N-th frame: a first DAS signal 402 (DAS (m)), a second DAS signal 401 (DAS(m−1)), and a second DAS signal 403 (DAS(m+1)). The first reference beam corresponds to C (m, n) calculated with Expression 1 where A (m, n) is the first DAS signal 402 and B (m, n) is a signal obtained by subtracting the second DAS signal 401 from the second DAS signal 403.

The second reference beam generating unit 22 generates the second reference beam from the following three DAS signals: the first DAS signal 402 (DAS(m)) calculated in the N-th frame, a second DAS signal 404 (DAS(m−2)) calculated in the (N−1)-th frame, and a second DAS signal 405 (DAS (m+2)) calculated in the (N+1)-th frame.

Here, the second reference beam corresponds to E (m, n) obtained with Expression 4 below where A (m, n) is the first DAS signal 402 and D (m, n) is a signal obtained by subtracting the second DAS signal 404 from the second DAS signal 405.

[Math. 4]

$$E(m,n) = \beta \cdot A(m,n) \cdot D(m,n) \qquad \text{Expression 4}$$

In other words, the signal E (m, n) is the product of the signal A (m, n), the signal D (m, n), and a predetermined coefficient β. The signal E (m, n) is obtained through matching of the stop band of the signal D to the profile of the signal A. The predetermined coefficient β is used to adjust narrowness of a beam profile, so that the beam profile of the signal E (m, n) matches that of the signal A (m, n).

The attenuation coefficient calculating unit 50 calculates an amplification factor G (m, n) based on the power signal of the signal A (m, n), the absolute value of the signal C (m, n), and the absolute value of the signal E (m, n). In other words, the attenuation coefficient calculating unit 50 calculates an attenuation coefficient based on Expression 5 below,

[Math. 5]

$$G(m,n) = \frac{|A(m,n)|^2 - |C(m,n)| - |E(m,n)|}{|A(m,n)|^2} \qquad \text{Expression 5}$$

Finally, the beamforming unit 60 generates the beamformed signal F (m, n) by multiplying the signal A (m, n) and the amplification factor G (m, n).

[Math. 6]

$$F(m,n) = A(m,n) \cdot G(m,n) \qquad \text{Expression 6}$$

The above features make it possible to generate a beamformed signal using five DAS signals even though only three DAS signal are calculated in a single frame (at one time point). The beamformed signal generated of the five DAS signals achieves a further improvement in the image quality of an ultrasound image than a beamformed signal generated of three DAS signals does.

Figure 15:
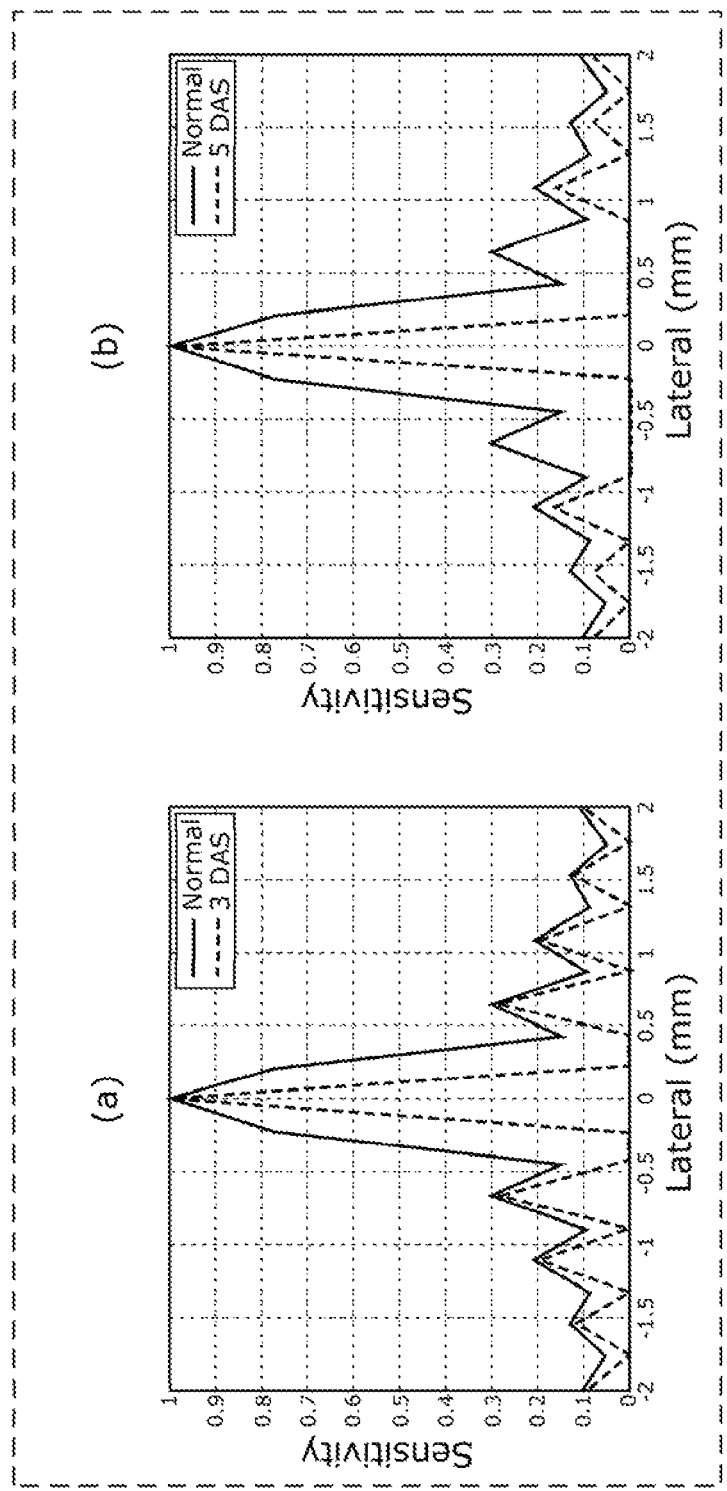
FIG. 15 depicts the beam profiles of beamformed signals generated by the beamforming unit according to Embodiment 1.

FIG. 15 depicts the beam profiles of beamformed signals generated by the beamforming unit 505 according to Embodiment 1.

The illustration (a) in FIG. 15 shows in a solid line the beam profile of a beamformed signal generated from one conventional DAS signal. The illustration (a) in FIG. 15 also shows in a dashed line the beam profile of a beamformed signal generated using three DAS signals by the beamforming unit 505a in FIG. 9.

The illustration (b) in FIG. 15 shows in a solid line the beam profile of a beamformed signal generated from one conventional DAS signal. The illustration (b) in FIG. 15 also shows in a dashed line the beam profile of a beamformed signal generated by the beamforming unit 505 in FIG. 12 using five DAS signals.

A comparison between the beam profile in the dashed line in the illustration (a) in FIG. 15 and the beam profile in the dashed line in the illustration (b) in FIG. 15 shows that, in the latter beam profile, unnecessary signal components, especially the ones found at the points of a margin of plus or minus 0.7 mm, have been removed. In other words, the beamforming unit 505 can achieve a further improvement in the image quality of an ultrasound image than the beamforming unit 505a does.

It is noted that the beamforming unit 505 generates more reference beams; however; the amount of calculations for generating the reference beams is significantly smaller than the amount of DAS operations. Hence, the beamforming unit 505 requires just a small amount of calculations in addition to three DAS operations in order to generate a beamformed signal which is as effective as one generated through five DAS operations.

It is noted that, in Embodiment 1, Expressions 1 and 4 show that the first and the second reference beams are the signals obtained by multiplication of the predetermined coefficients α and β. Instead, the predetermined coefficients α and β do not have to be multiplied in Expressions 1 and 4. Here, the predetermined coefficients α and β may respectively be multiplied by the signal C (m, n) of the first reference beam and the signal E (m, n) of the second reference beam.

It is noted that, at the scan lines on the both end in an ultrasound image, a beamformed signal might not be generated using three or five DAS signals.

In the ultrasound image in FIG. 8, for example, the first and the n-th scan lines are on both ends. Thus, it is impossible to generate a beamformed signal from three DAS signals.

In such a case, that is the case where the target scan line in the N-th frame is the endmost scan line among the multiple scan lines, the beamforming unit 60 may provide, as the beamformed signal for the target scan line, the first DAS signal for the endmost scan line calculated by the DAS unit 10 in the N-th frame. Such a feature prevents the endmost image of an ultrasound image from missing.

Similarly, in the ultrasound image shown in FIG. 8, a beamforming signal can be generated from three DAS signal for the second and the (N−1)-th scan lines. However, it is impossible to generate a beamforming signal from five DAS signals.

In such a case, that is the case where the target scan line in the N-th frame is the second scan line from the endmost scan line among the multiple scan lines, the attenuation coefficient calculating unit 50 may calculate an attenuation coefficient determined based only on the first reference beam of the first and the second reference beams. The beamforming unit 60 may generate and provide the beamformed signal for the target scan line in the N-th frame, by multiplying the first DAS signal calculated in the N-th frame by the attenuation coefficient determined based only on the first reference beam.

Moreover, when the target scan line in the N-th frame is the second scan line from the endmost scan line among the multiple scan lines, the beamforming unit 60 may directly provide, as the beamformed signal for the target scan line, the first DAS signal calculated by the DAS unit 10 in the N-th frame for the second scan line from the endmost scan line.

Such a feature prevents the endmost image of an ultrasound image from missing.

Thanks to the above features, the beamforming unit 505 in Embodiment 1 can generate a beamformed signal using DAS signals for five scan lines while the DAS signals to be calculated are still for three scan lines for each frame. The beamforming unit 505 sees an increase in the amount of operations due to generation of a reference beam; however, the amount of the calculations is significantly smaller than the amount of DAS operations. Hence, the beamforming unit 505 allows the ultrasonic diagnostic apparatus 100 to achieve a reduction in the load of signal processing and an improvement in the resolution of an image.

Embodiment 2

In Embodiment 1, the beamforming unit 505 generates a beamformed signal using DAS signals for five scan lines while the DAS signals to be calculated are still for three scan lines for each frame. The beamforming unit, however, selectively executes a technique to generate a beamformed signal. Embodiment 2 describes an example of a beamforming unit which is capable of selectively executing a technique to generate a beamformed signal.

Figure 16:
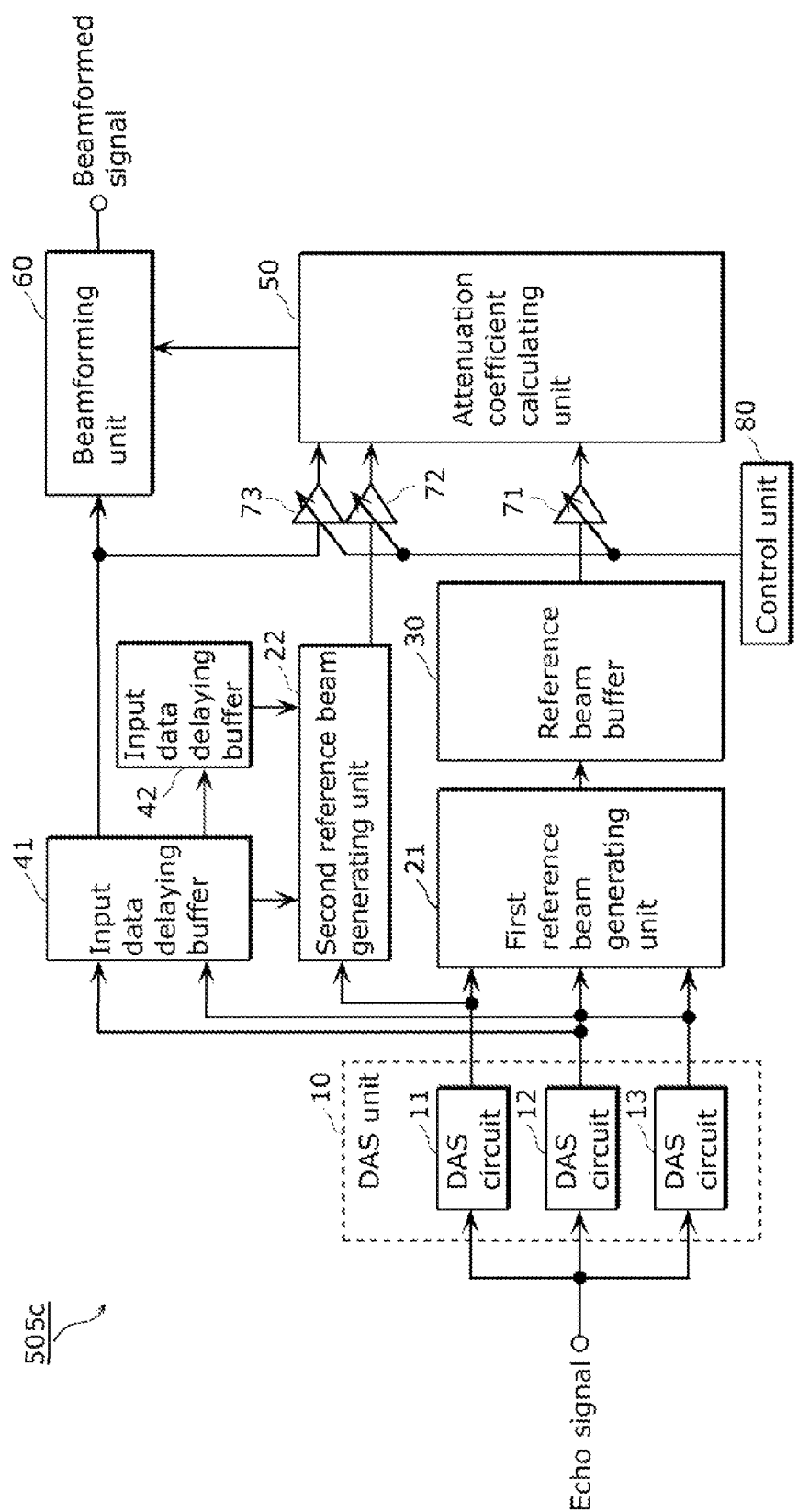
FIG. 16 depicts a block diagram showing a structure of a beamforming unit according to Embodiment 2.

FIG. 16 depicts a block diagram showing a structure of a beamforming unit according to Embodiment 2. In FIG. 16, the same constituent elements as the ones in FIG. 12 have the same reference signs, and the details thereof shall be omitted.

A beamforming unit 505c in FIG. 16 differs from the beamforming unit 505 in FIG. 12 in that the former includes a control unit 80 and multiplying circuits 71 to 73. In FIG. 16, the control unit 80 and the multiplying circuits 71 to 73 are provided separately from the attenuation coefficient calculating unit 50; instead, the control unit 80 and the multiplying circuits 71 to 73 may be implemented as a function of the attenuation coefficient calculating unit 50.

The control unit 80 sets a coefficient for the multiplying circuits 71 to 73.

The multiplying circuit 71 multiplies the first reference beam stored in the reference beam buffer 30 by a coefficient, and provides the product to the attenuation coefficient calculating unit 50. Here, the coefficient that multiplied by the multiplying circuit 71 is the predetermined coefficient α.

The multiplying circuit 72 multiplies the second reference beam generated by the second reference beam generating unit 22 by a coefficient, and provides the product to the attenuation coefficient calculating unit 50. Here, the coefficient that multiplied by the multiplying circuit 72 is the predetermined coefficient β.

The multiplying circuit 73 multiplies the first DAS signal stored in the input data delaying buffer 41 by a coefficient, and provides the product to the attenuation coefficient calculating unit 50. In other words, a coefficient (hereinafter referred to as a predetermined coefficient γ) may be multiplied by the signal A (m, n) in Expression 5.

The control unit 80 sets each of the predetermined coefficients α, β, and γ based on, for example, the number of target scan line. In the case where the target scan line is the endmost scan line, the control unit 80 sets $\alpha=\beta=0$ and $\gamma=1$. Hence, the attenuation coefficient to be calculated by the attenuation coefficient calculating unit 50 is 1, and the beamforming unit 60 directly provides the first DAS signal for the target scan line as the beamformed signal for the target scan line. It is noted that the attenuation coefficient is 1 means that the attenuation coefficient is the one that leaves the first DAS signal unchanged.

In the case where the target scan line is the second scan line from the endmost, for example, the control unit 80 sets $\alpha \neq 0$, $\beta=0$, and $\gamma=0$. Hence, the attenuation coefficient to be calculated by the attenuation coefficient calculating unit 50 is the one obtained with Expression 2. In other words, the beamforming unit 60 generates a beamformed signal based on the attenuation coefficient calculated using three DAS signals.

As described above, the control unit 80 and the multiplying circuits 71 to 73 make it possible to adjust, for each of the target scan lines, the number of the DAS signals to be used for calculating the attenuation coefficients.

In other words, when the control unit 80 and the multiplying circuits 71 to 73 are implemented as a function of the attenuation coefficient calculating unit 50, the attenuation coefficient calculating unit 50 can selectively execute, based on the number of target scan line in the N-th frame, (i) calculation of an attenuation coefficient based on both the first and the second reference beams, (ii) calculation of the attenuation coefficient based only on the first reference beam of the first and the second reference beams, and (iii) calculation of the attenuation coefficient to be 1.

It is noted that the control unit 80 may set each of the predetermined coefficients $\alpha$, $\beta$, and $\gamma$ based on the "depth" that is the distance found in a target scan line and stretching between the surface of the subject 204 and the focal point of an ultrasound wave transmitted by the transmitting unit (the length in the "depth" direction illustrated in FIG. 8). In other words, the "depth" is the distance between the positions of the multiple receiving elements and the point included in the subject 204 and where ultrasound signals (reflective waves) start to bounce off the subject 204.

In general, when the depth is great (far), the frequency of the ultrasound waves transmitted by the transmitting unit needs to be set lower. Thus, the beamformed signal tends to be wider in beam profile. Hence, when the depth is great, it is desirable to generate the beamformed signal using five DAS signals. In other words, it is desirable for the attenuation coefficient calculating unit 50 to calculate an attenuation coefficient based on both the first and the second reference beams.

In contrast, when the depth is small (short), the frequency of the ultrasound waves transmitted by the transmitting unit is set higher so that the beam profile of the beamformed signal is formed narrower.

In such a case, it is desirable from a standpoint of an amount of calculations to use one or three DAS signals to generate the beamformed signal. In other words, it is desirable for the attenuation coefficient calculating unit 50 to either calculate an attenuation coefficient based only on the first reference beam of the first and the second reference beams or calculate the attenuation coefficient to be 1.

As described above, the control unit 80 and the multiplying circuits 71 to 73 make it possible to adjust the number of the DAS signals to be used for calculation of an attenuation coefficient, depending on the "depth" of a target scan line. Specifically, a greater depth of the target scan line makes it possible to execute control for generating a beamformed signal using more DAS signals.

It is noted that a technique to calculate an attenuation coefficient can be selectively executed based on whether or not the depth is greater than or equal to a threshold.

Here, when the control unit 80 and the multiplying circuits 71 to 73 are implemented as a function of the attenuation coefficient calculating unit 50, the attenuation coefficient calculating unit 50 calculates an attenuation coefficient based on both the first and the second reference beams in the case where the depth of the target scan line is greater than or equal to a first threshold. The attenuation coefficient calculating unit 50 calculates the attenuation coefficient based only on the first reference beam of the first and the second reference beams in the case where the depth of the target scan line is smaller than the first threshold and greater than or equal to a second threshold which is smaller than the first threshold. Furthermore, the attenuation coefficient calculating unit 50 calculates the attenuation coefficient to be 1 when the depth of the target scan line is smaller than the second threshold.

As described above, the beamforming unit 505c according to Embodiment 2 can adaptively select a technique to calculate an attenuation coefficient, based on the position and the depth of a target scan line.

Other Embodiment

The present disclosure has been described based on the above exemplary embodiments; however, the present disclosure also encompasses the embodiments. The cases below are also regarded as a scope of the present disclosure.

In the embodiments, the DAS unit 10 generates three DAS signals for each frame, and the attenuation coefficient calculating unit 50 calculates an attenuation coefficient from five DAS signals. However, for example, the DAS unit 10 may generate five DAS signals for each frame, and the attenuation coefficient calculating unit 50 may calculate an attenuation coefficient from seven DAS signals. In other words, the present disclosure can be implemented when the DAS unit 10 generates 2k+1 DAS signals where k is a positive integer or an integer of 1 or greater, and the attenuation coefficient calculating unit 50 calculates an attenuation coefficient from the 2k+1 DAS signals.

Each of the constituent elements in the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory. Here, the software program for implementing the ultrasonic diagnostic apparatus (beamformer) according to each of the embodiments is a program described below.

The program causes a computer to execute a beamforming method for generating beamformed signals, each corresponding to one of scan lines for generating an ultrasound image, from echo signals generated from ultrasound signals bounced off a subject and received by receiving elements. The beamforming method includes: determining, for each of frames, one of the scan lines, in a sorting order determined in a given direction, as a target scan line for the frame and select 2k+1 scan lines (k is a positive integer) included in the scan lines and aligned in a row with the target scan line positioned in a middle, and performing, for each of the frames, a DAS operation on each of the echo signals to calculate a first DAS signal which is a DAS signal for the target scan line and second DAS signals which are DAS signals each for one of the selected 2k+1 scan lines other than the target scan line; generating a first reference beam from the first DAS signal and the second DAS signals all of which are calculated in an N-th frame of the frames; generating a second reference beam from (i) one of the second DAS signals which is calculated in an (N−1)-th frame of the frames immediately preceding the N-th frame and is generated for one of the scan lines which has an earliest number in the sorting order, (ii) the first DAS signal which is calculated in the N-th frame and (iii) another one of the second DAS signals which is calculated in an (N+1)-th frame of the frames immediately succeeding the N-th frame and is generated for another one of the scan lines which has a latest number in the sorting order; calculating, based on the first reference beam and the second reference beam, an attenuation coefficient for forming narrower a profile of the first DAS signal calculated in the N-th frame; and generating and providing a beamformed signal included in the beamformed signals and generated for the target scan line in the N-th frame, by multiplying the first DAS signal calculated in the N-th frame by the attenuation coefficient.

The herein disclosed subject matter is to be considered descriptive and illustrative only, and the appended Claims are of a scope intended to cover and encompass not only the particular embodiments disclosed, but also equivalent structures, methods, and/or uses.

INDUSTRIAL APPLICABILITY

One or more exemplary embodiments disclosed herein are applicable to an ultrasonic diagnostic apparatus which performs beamforming using many DAS signals to achieve high resolution and improves the image duality of an ultrasound image.

The invention claimed is:
1. An ultrasonic diagnostic apparatus comprising
a beamformer which generates beamformed signals, each corresponding to one of scan lines for generating an ultrasound image, from echo signals generated from ultrasound signals bounced off a subject and received by receiving elements,
wherein the beamformer includes:
a delay-and-sum (DAS) unit configured, for each of frames, to (i) determine one of the scan lines, in a sorting order determined in a given direction, as a target scan line for the frame and select 2k+1 scan lines included in the scan lines and aligned in a row with the target scan line positioned in a middle of the scan lines, and (ii) perform a DAS operation on each of the echo signals to calculate a first DAS signal which is a DAS signal for the target scan line and second DAS signals which are DAS signals each for one of the selected 2k+1 scan lines other than the target scan line, where k is a positive integer;
a first reference beam generating unit configured to generate a first reference beam from the first DAS signal and the second DAS signals all of which are calculated in an N-th frame of the frames;
a second reference beam generating unit configured to generate a second reference beam from (i) one of the second DAS signals which is calculated in an (N−1)-th frame of the frames immediately preceding the N-th frame and is generated for one of the scan lines which has an earliest number in the sorting order among the selected 2k+1 scan lines, (ii) the first DAS signal which is calculated in the N-th frame, and (iii) another one of the second DAS signals which is calculated in an (N+1)-th frame of the frames immediately succeeding the N-th frame and is generated for another one of the scan lines which has a latest number in the sorting order among the selected 2k+1 scan lines;
an attenuation coefficient calculating unit configured to calculate, based on the first reference beam and the second reference beam, an attenuation coefficient for forming narrower a profile of the first DAS signal calculated in the N-th frame; and
a beamforming unit configured to generate and provide a beamformed signal included in the beamformed signals and generated for the target scan line in the N-th frame, by multiplying the first DAS signal calculated in the N-th frame by the attenuation coefficient.

2. The ultrasonic diagnostic apparatus according to claim 1,
wherein, for each of the frames, the DAS unit is configured to select three scan lines included in the scan lines and aligned in a row with the target scan line positioned in a middle of the selected three scan lines, and calculate the first DAS signal and the second DAS signals, the second DAS signals each being generated for one of two scan lines included in the three scan lines, and the two scan lines each neighboring the target scan line, and
wherein the first reference beam generating unit is configured to generate the first reference beam from the first DAS signal and two second DAS signals all of which are calculated in the N-th frame, the two second DAS signals being the second DAS signals each generated for one of the two scan lines.

3. The ultrasonic diagnostic apparatus according to claim 1, wherein, in a case where the target scan line in the N-th frame is either an endmost scan line among the scan lines for generating the ultrasound image or a second scan line from the endmost scan line among the scan lines for generating the ultrasound image, the beamforming unit is configured to provide the first DAS signal calculated in the N-th frame as the beamformed signal for the target scan line in the N-th frame.

4. The ultrasonic diagnostic apparatus according to claim 1, wherein, in a case where the target scan line in the N-th frame is a second scan line from an endmost scan line among the scan lines for generating the ultrasound image, the attenuation coefficient calculating unit is configured to calculate the attenuation coefficient determined based only on the first reference beam of the first reference beam and the second reference beam, and the beamforming unit is configured to generate and provide the beamformed signal for the target scan line in the N-th frame, by multiplying the first DAS signal calculated in the N-th frame by the attenuation coefficient determined based only on the first reference beam.

5. The ultrasonic diagnostic apparatus according to claim 2,
wherein the first reference beam generating unit is configured to generate the first reference beam by multiplying the first DAS signal calculated in the N-th frame by a difference between the two second DAS signals calculated in the N-th frame, and
wherein the second reference beam generating unit is configured to generate the second reference beam by multiplying the first DAS signal calculated in the N-th frame by a difference between the one second DAS signal and the other second DAS signal, the one second DAS signal being calculated in the (N−1)-th frame and generated for the one scan line having the earliest number in the sorting order among the selected 2k+1 scan lines and the other second DAS signal being calculated in the (N+1)- th frame and generated for the other scan line having the latest number in the sorting order among the selected 2k+1 scan lines.

6. The ultrasonic diagnostic apparatus according to claim 2,
wherein the first reference beam generating unit is configured to generate the first reference beam as a product of a difference between the two second DAS signals calculated in the N-th frame, the first DAS signal calculated in the N-th frame, and a predetermined coefficient α, and
wherein the second reference beam generating unit is configured to generate the second reference beam as a product of a difference between the one second DAS signal and the other second DAS signal, the first DAS signal calculated in the N-th frame, and a predetermined coefficient β, the one second DAS signal being calculated in the (N−1)-th frame and generated for the one scan line having the earliest number in the sorting order among the selected 2k+1 scan lines and the other second DAS signal being calculated in the (N+1)-th frame and generated for the other scan line having the latest number in the sorting order among the selected 2k+1 scan lines.

7. The ultrasonic diagnostic apparatus according to claim 6, wherein the attenuation coefficient calculating unit configured to calculate G which is the attenuation coefficient, using an expression below, where A is the first DAS signal calculated in the N-th frame, C is the first reference beam, and E is the second reference beam:

$$G(m, n) = \frac{|A|^2 - |C| - |E|}{|A|^2}.$$ [Math. 1]

8. The ultrasonic diagnostic apparatus according to claim 1,
wherein the attenuation coefficient calculating unit is configured to, based on a distance between positions of the receiving elements and a point where the ultrasound signals start to bounce off, selectively execute (i) calculation of the attenuation coefficient based on both the first reference beam and the second reference beam, (ii) calculation of the attenuation coefficient based only on the first reference beam of the first reference beam and the second reference beam, and (iii) calculation of the attenuation coefficient to be 1.

9. The ultrasonic diagnostic apparatus according to claim 1,
wherein, the attenuation coefficient calculating unit is configured to, based on a number of the target scan line in the sorting order in the N-th frame, selectively execute (i) calculation of the attenuation coefficient based on both the first reference beam and the second reference beam, (ii) calculation of the attenuation coefficient based only on the first reference beam of the first reference beam and the second reference beam, and (iii) calculation of the attenuation coefficient to be 1.

10. A beamforming method for generating beamformed signals, each corresponding to one of scan lines for generating an ultrasound image, from echo signals generated from ultrasound signals bounced off a subject and received by receiving elements, the beamforming method comprising:
determining, for each of frames, one of the scan lines, in a sorting order determined in a given direction, as a target scan line for the frame and select 2k+1 scan lines included in the scan lines and aligned in a row with the target scan line positioned in a middle of the selected 2k+1 scan lines, and performing, for each of the frames, a DAS operation on each of the echo signals to calculate a first DAS signal which is a DAS signal for the target scan line and second DAS signals which are DAS signals each for one of the selected 2k+1 scan lines other than the target scan line, where k is a positive integer;
generating a first reference beam from the first DAS signal and the second DAS signals all of which are calculated in an N-th frame of the frames;
generating a second reference beam from (i) one of the second DAS signals which is calculated in an (N−1)-th frame of the frames immediately preceding the N-th frame and is generated for one of the scan lines which has an earliest number in the sorting order among the selected 2k+1 scan lines, (ii) the first DAS signal which is calculated in the N-th frame, and (iii) another one of the second DAS signals which is calculated in an (N+1)-th frame of the frames immediately succeeding the N-th frame and is generated for another one of the scan lines which has a latest number in the sorting order among the selected 2k+1 scan lines;
calculating, based on the first reference beam and the second reference beam, an attenuation coefficient for forming narrower a profile of the first DAS signal calculated in the N-th frame; and
generating and providing a beamformed signal included in the beamformed signals and generated for the target scan line in the N-th frame, by multiplying the first DAS signal calculated in the N-th frame by the attenuation coefficient.

11. A non-transitory computer-readable recording medium having stored thereon a computer program that is executable by a computer to cause the computer to execute a beamforming method for generating beamformed signals, each corresponding to one of scan lines for generating an ultrasound image, from echo signals generated from ultrasound signals bounced off a subject and received by receiving elements, the program causing the computer to perform functions of the beamforming method comprising:
determining, for each of frames, one of the scan lines, in a sorting order determined in a given direction, as a target scan line for the frame and select 2k+1 scan lines included in the scan lines and aligned in a row with the target scan line positioned in a middle of the selected 2k+1 scan lines, and performing, for each of the frames, a DAS operation on each of the echo signals to calculate a first DAS signal which is a DAS signal for the target scan line and second DAS signals which are DAS signals each for one of the selected 2k+1 scan lines other than the target scan line, where k is a positive integer;
generating a first reference beam from the first DAS signal and the second DAS signals all of which are calculated in an N-th frame of the frames;
generating a second reference beam from (i) one of the second DAS signals which is calculated in an (N−1)-th frame of the frames immediately preceding the N-th frame and is generated for one of the scan lines which has an earliest number in the sorting order among the selected 2k+1 scan lines, (ii) the first DAS signal which is calculated in the N-th frame, and (iii) another one of the second DAS signals which is calculated in an (N+1)-th frame of the frames immediately succeeding the N-th frame and is generated for another one of the scan lines which has a latest number in the sorting order among the selected 2k+1 scan lines;

calculating, based on the first reference beam and the second reference beam, an attenuation coefficient for forming narrower a profile of the first DAS signal calculated in the N-th frame; and generating and providing a beamformed signal included in the beamformed signals and generated for the target scan line in the N-th frame, by multiplying the first DAS signal calculated in the N-th frame by the attenuation coefficient.

12. An integrated circuit which generates beamformed signals, each corresponding to one of scan lines for generating an ultrasound image, from echo signals generated from ultrasound signals bounced off a subject and received by receiving elements, the circuit comprising:

a DAS unit configured, for each of frames, to (i) determine one of the scan lines, in a sorting order determined in a given direction, as a target scan line for the frame and select 2k+1 scan lines included in the scan lines and aligned in a row with the target scan line positioned in a middle of the selected 2k+1 scan lines, and (ii) perform a DAS operation on each of the echo signals to calculate a first DAS signal which is a DAS signal for the target scan line and second DAS signals which are DAS signals each for one of the selected 2k+1 scan lines other than the target scan line, where k is a positive integer;

a first reference beam generating unit configured to generate a first reference beam from the first DAS signal and the second DAS signals all of which are calculated in an N-th frame of the frames;

a second reference beam generating unit configured to generate a second reference beam from (i) one of the second DAS signals which is calculated in an (N−1)-th frame of the frames immediately preceding the N-th frame and is generated for one of the scan lines which has an earliest number in the sorting order among the selected 2k+1 scan lines, (ii) the first DAS signal which is calculated in the N-th frame and (iii) another one of the second DAS signals which is calculated in an (N+1)-th frame of the frames immediately succeeding the N-th frame and is generated for another one of the scan lines which has a latest number in the sorting order among the selected 2k+1 scan lines;

an attenuation coefficient calculating unit configured to calculate, based on the first reference beam and the second reference beam, an attenuation coefficient for forming narrower a profile of the first DAS signal calculated in the N-th frame; and a beamforming unit configured to generate and provide a beamformed signal included in the beamformed signals and generated for the target scan line in the N-th frame, by multiplying the first DAS signal calculated in the N-th frame by the attenuation coefficient.

* * * * *